(12) United States Patent
Lewis et al.

(10) Patent No.: US 11,492,390 B2
(45) Date of Patent: Nov. 8, 2022

(54) MUTANT ALPHA-1-ANTITRYPSIN COMPOSITIONS AND USE THEREOF

(71) Applicant: B. G. NEGEV TECHNOLOGIES AND APPLICATIONS LTD., AT BEN-GURION UNIVERSITY, Beer-Sheva (IL)

(72) Inventors: Eli Chaim Lewis, Be'er Sheva (IL); Yotam Lior, Be'er Sheva (IL)

(73) Assignee: B. G. NEGEV TECHNOLOGIES AND APPLICATIONS LTD., AT BEN-GURION UNIVERSITY, Beer Sheva (IL)

( * ) Notice: Subject to any disclaimer, the term of this patent is extended or adjusted under 35 U.S.C. 154(b) by 26 days.

(21) Appl. No.: 16/499,534

(22) PCT Filed: Apr. 2, 2018

(86) PCT No.: PCT/IL2018/050385
§ 371 (c)(1),
(2) Date: Sep. 30, 2019

(87) PCT Pub. No.: WO2018/185756
PCT Pub. Date: Oct. 11, 2018

(65) Prior Publication Data
US 2020/0140524 A1 May 7, 2020

Related U.S. Application Data

(60) Provisional application No. 62/480,480, filed on Apr. 2, 2017.

(51) Int. Cl.
*C07K 14/81* (2006.01)
*A61P 17/02* (2006.01)
*A61P 29/00* (2006.01)
*A61K 38/00* (2006.01)

(52) U.S. Cl.
CPC .......... *C07K 14/8125* (2013.01); *A61P 17/02* (2018.01); *A61P 29/00* (2018.01); *A61K 38/00* (2013.01)

(58) Field of Classification Search
CPC ...... C07K 14/8125; A61P 17/02; A61P 29/00; A61K 38/00
See application file for complete search history.

(56) References Cited

U.S. PATENT DOCUMENTS

| 6,638,909 B1 | 10/2003 | Grady et al. | |
| 2012/0094356 A1* | 4/2012 | Chung | C07K 14/8125 435/188 |
| 2017/0334971 A1* | 11/2017 | Shaw | A61P 3/04 |

FOREIGN PATENT DOCUMENTS

| WO | WO 2009/066807 | * | 5/2009 | ............ C07K 14/00 |
| WO | 2010123290 A2 | | 10/2010 | |
| WO | WO 2016/102580 | * | 6/2016 | ........... C07K 14/495 |

OTHER PUBLICATIONS

Nukiwa et al., 1986, Identification of a Second Mutation in the Protein-coding Sequence of the Z type Alpha 1-Antitrypsin Gene, The Journal of Biological Chemistry, 261(34): 15989-15994.*
Gierczak et al., 2015, Comparison of mammalian and bacterial expression library screening to detect recombinant alpha-1 proteinase inhibitor variants with enhanced thrombin inhibitory capacity, Journal of Biotechnology, 208: 54-62.*
Schapira et al., 1987, Protection by Recombinant alpha1-Antitrypsin Ala357 Arg358 against Arterial Hypotension Induced by Factor XII Fragment, J Clin Invest, 80: 582-585.*
Bischoff et al., 1991, Purification and Biochemical Characterization of Recombinantalpha1-Antitrypsin Variants Expressed in *Escherichia coli*, Biochemistry, 30: 3464-3472 (provided by applicants in the IDS).*
Patston et al., 1990, Reactivity of alpha1-Antitrypsin Mutants against Proteolytic Enzymes of the Kallikrein-Kinin, Complement, and Fibrinolytic Systems, The Journal of Biological Chemistry, 265(18): 10786-10791.*
Stephens AW, Thalley BS, Hirs CH. Antithrombin-III Denver, a reactive site variant. The Journal of biological chemistry (1987) 262(3):1044-8.
Ozeri E, Mizrahi M, Shahaf G, Lewis EC. alpha-1 antitrypsin promotes semimature, IL-10-producing and readily migrating tolerogenic dendritic cells. The Journal of Immunology (2012) 189(1):146-53.
Subramanian S, Shahaf G, Ozeri E, Miller LM, Vandenbark AA, Lewis EC, et al. Sustained expression of circulating human alpha-1 antitrypsin reduces inflammation, increases CD4+FoxP3+ Treg cell population and prevents signs of experimental autoimmune encephalomyelitis in mice. Metabolic brain disease (2011) 26(2):107-13.
Bischoff R, Speck D, Lepage P, Delatre L, Ledoux C, Brown SW, et al. Purification and biochemical characterization of recombinant alpha 1-antitrypsin variants expressed in *Escherichia coli*. Biochemistry (1991) 30(14):3464-72.
Agarwal S, Singh R, Sanyal I, Amla DV. Expression of modified gene encoding functional human alpha-1-antitrypsin protein in transgenic tomato plants. Transgenic research (2008) 17(5):881-96.
Yotam Lior, Assaf Geyra et al., "Therapeutic compositions and uses of alpha1-antitrypsin: a patent review (2012-2015)", Expert Opinion on Therapeutic Patents, May 2016, 26(5):581-9.
Angelia D. Lockett et al., "α1-Antitrypsin Modulates Lung Endothelial Cell Inflammatory Responses to TNF-α", American Journal of Respiratory Cell and Molecular Biology, Jul. 2013; 49(1): 143-150.
Database Blast NCBI [online], Accession No. 2QUG_A <https://www.ncbi.nlm.nih.gov/protein/2QUG_A?report=genbank&log$=protalign&blast_rank=9&RID=GWKCE32401R> Oct. 31, 2012 (Oct. 31, 2012).
Database Blast NCBI [online], Accession No. 3NE4 A <https://www.ncbi.nlm.nih.gov/protein/3NE4_A?report=genbank&log$=protalign&blast_rank=5&RID=HEZRU56J015> Oct. 10, 2012 (Oct. 10, 2012).

(Continued)

Primary Examiner — Amber D Steele
(74) Attorney, Agent, or Firm — The Roy Gross Law Firm, LLC; Roy Gross

(57) ABSTRACT

The present invention provides mutant alpha 1-antitrypsin proteins, pharmaceutical compositions comprising the same, and methods of use thereof in treatment of subjects with an inflammatory disease or disorder.

12 Claims, 12 Drawing Sheets

Specification includes a Sequence Listing.

(56) References Cited

OTHER PUBLICATIONS

Database Blast NCBI [online], Accession No. ABV21360 <https://www.ncbi.nlm.nih.gov/protein/ABV21360?report=genbank&log$=protalign&blast_rank=3&RID=HEZRU56J015> Jun. 26, 2016 (Jun. 26, 2016).

Database Blast NCBI [online], Accession No. 2D26_A <https://www.ncbi.nlm.nih.gov/protein/2D26_A?report=genbank&log$=protalign&blast_rank=61&RID=H78C6WZ401R> Oct. 10, 2012 (Oct. 10, 2012).

Danny Jonigk et al, "Anti-inflammatory and immunomodulatory properties of α1-antitrypsin without inhibition of elastase", Proceedings of the National Academy of Sciences of the United States of America, Sep. 10, 2013;110(37):15007-12.

Guttman et al., "Alpha1-antitrypsin, an endogenous immunoregulatory molecule: distinction between local and systemic effects on tumor immunology", Integr Cancer Sci Therap, 2016, vol. 2(6):272-280.

Dabbagh et al. "Alpha-1-antitrypsin stimulates fibroblast proliferation and procollagen production and activates classical MAP kinase signalling pathways", Journal of Cellular Physiology, Jan. 2001;186(1):73-81.

Sabina Janciauskiene et al., "Well-Known and Less Well-Known Functions of Alpha-1 Antitrypsin. Its Role in Chronic Obstructive Pulmonary Disease and Other Disease Developments", Annals of the American Thoracic Society, Aug. 2016;13 Suppl 4:S280-8.

\* cited by examiner

Figure 1A
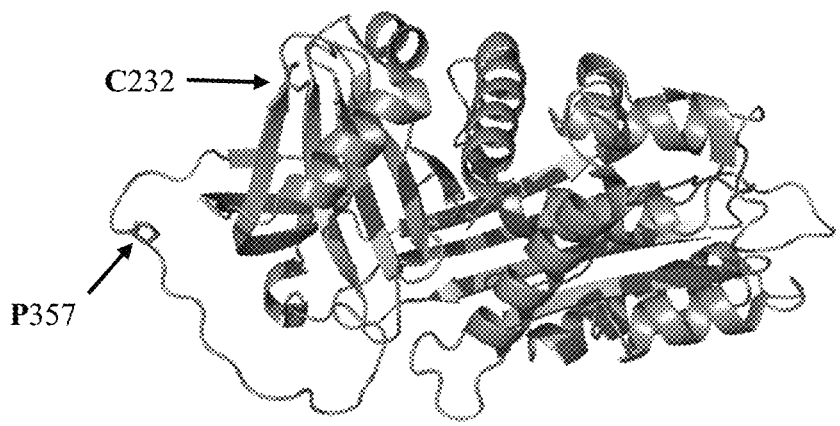
Figure 1B
| | | | |
|---|---|---|---|
| WT | ---- MFNIQH<u>C</u>KKLSSW ---- | MFLEAI<u>P</u>MSIPPE ---- | SEQ ID NO: 2 |
| C232P | ---- MFNIQH<u>P</u>KKLSSW ---- | MFLEAIPMSIPPE ---- | SEQ ID NO: 3 |
| P357C | ---- MFNIQHCKKLSSW ---- | MFLEAI<u>C</u>MSIPPE ---- | SEQ ID NO: 4 |
| P357A | ---- MFNIQHCKKLSSW ---- | MFLEAI<u>A</u>MSIPPE ---- | SEQ ID NO: 5 |
Figure 1C
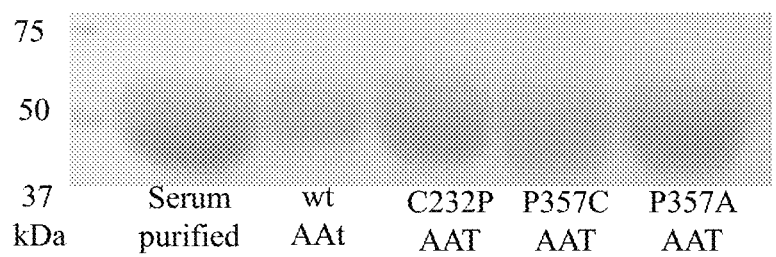
Figure 1D
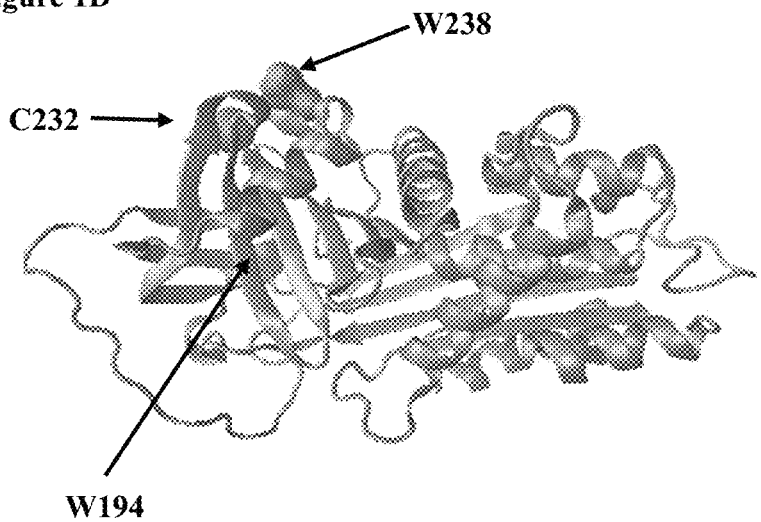

MUTANT ALPHA-1-ANTITRYPSIN COMPOSITIONS AND USE THEREOF

CROSS REFERENCE TO RELATED APPLICATIONS

This application claims the benefit of priority of U.S. Provisional Patent Application No. 62/480,480, filed Apr. 2, 2017, the contents of which are incorporated herein by reference in their entirety.

FIELD OF INVENTION

The present invention relates to a mutant form of α1-antitrypsin, compositions comprising same, and use thereof.

BACKGROUND OF THE INVENTION

Human alpha1-antitrypsin (hAAT) is a 52 kDa, 394-amino acid glycoprotein, and a member of the serine protease inhibitor (SERPIN) family. The molecule is secreted to the circulation primarily by hepatocytes, both in steady state and during the acute phase response (a response to inflammation). Additionally, local synthesis of hAAT is carried-out by lung epithelia, intestinal paneth cells and M2-like macrophages. While globular in structure, hAAT has a reactive center loop (RCL, amino acid positions 357-366) protruding from its surface, acting as a sequence-specific bait for serine-proteases, among which are neutrophil elastase, cathepsin G and proteinase-3. RCL cleavage leads to covalent attachment of the targeted protease to hAAT, followed by a conformational change and the removal of the hAAT: protease complex from the circulation, thus creating protease inhibition.

Interestingly, proteases outside the serine-protease family are also inhibited by hAAT, albeit to a lesser extent. As such, it has been proposed that the globular surface of hAAT may contain significant functional attributes. Furthermore, certain activities attributed to hAAT appear to be reproducible in formulations that lack elastase inhibition.

The breadth of anti-inflammatory and immunomodulatory functions of hAAT is increasingly recognized. hAAT promotes production of anti-inflammatory cytokines, such as IL-10 and IL-1 receptor antagonist (IL-1Ra), and inhibits release of pro-inflammatory cytokines and chemokines, such as IL-6 and TNFα. In the context of allograft transplantation, hAAT modifies dendritic cell responses and B lymphocyte activities, reduces the levels of inducible co-stimulatory molecules, e.g., CD40 and CD86, and promotes regulatory T cell expansion. Of particular interest, hAAT reduces soluble TNFα levels and interferes with TNFα-dependent responses. Inducible membrane-associated TNFα appears to accumulate on the surface of hAAT-treated leukocytes, even though its cleavage requires ADAM metallopeptidase domain 17 (ADAM17/TACE), which is outside the repertoire of hAAT protease inhibition.

Mutations within the RCL usually deprive hAAT of its protease-inhibiting capacity, as in the case of replacing proline with cysteine at position 357 (pro357cys). However, little is known regarding the effects of this and other mutations outside the RCL in as far as the anti-inflammatory properties of hAAT are concerned.

SUMMARY OF THE INVENTION

The present invention provides isolated polypeptides comprising an alpha1-antitrypsin (AAT) mutant. The invention also provides pharmaceutical compositions comprising the polypeptides of the invention as well as methods of use thereof.

According to a first aspect, there is provided an isolated polypeptide comprising the amino acid sequence set forth in SEQ ID NO: 1, or a fragment, a derivative or an analog thereof, wherein X is any amino acid other than cysteine.

According to one embodiment, the analog comprises at least 70% homology to SEQ ID NO: 2.

According to one embodiment, X is selected from the group consisting of: proline, valine, threonine, serine and isoleucine. According to one embodiment, X is proline According to one embodiment, the polypeptides of the invention further comprise a mutation at position 357, wherein a proline is mutated to any amino acid other than proline or is an absent amino acid. According to one embodiment, the proline is mutated to an absent amino acid. According to one embodiment, the proline is mutated to an amino acid selected from the group consisting of: cysteine, alanine, methionine, isoleucine, and valine. According to one embodiment, the proline is mutated to an amino acid selected form cysteine and alanine.

According to one embodiment, the polypeptides on the invention have at least one therapeutic property that is greater than the therapeutic property of rhAAT (SEQ ID NO: 2) or serum purified hAAT. According to one embodiments, the therapeutic property is selected from an anti-inflammatory property and a wound healing property. According to one embodiment, the anti-inflammatory property is selected from reducing secretion of a pro-inflammatory cytokine and reducing activation of macrophages. According to one embodiment the pro-inflammatory cytokine is selected from IL-6 and TNF-α. According to one embodiments, the wound healing property is selected from increasing the rate of wound closure and inducing wound closure to begin sooner.

According to one embodiment, the polypeptides of the invention are pharmacokinetically advantageous as compared to rhAAT protein (SEQ ID NO: 2) or serum purified hAAT. According to one embodiment, the pharmacokinetically advantageous polypeptide comprises one or more properties selected from: increased serum stability, increased distribution, and increased bioavailability.

By another aspect, there is provided a pharmaceutical composition comprising any one of the polypeptides of the invention and a pharmaceutically acceptable carrier or excipient.

By another aspect, there is provided a method of treating, ameliorating or preventing an inflammatory-associated disease or disorder in a subject in need thereof, the method comprising administering to the subject a therapeutically acceptable amount of any one of the pharmaceutical compositions of the invention, thereby treating, ameliorating or preventing the inflammatory-associated disease or disorder in the subject.

By another aspect, there is provided a method of treating a wound in a subject in need thereof, the method comprising administering to the subject a therapeutically acceptable amount of any one of the pharmaceutical compositions of the invention, thereby treating a wound in the subject.

According to one embodiment, the inflammatory-associated disease or disorder is selected from the group consisting of: diabetes, allogenic and xenogeneic transplantation, graft-versus-host disease, myocardial infarction, radiation exposure, chronic fatigue syndrome, bacterial infection, inflammatory bowel disease, rheumatoid arthritis, liver disease, radiation exposure, osteoporosis, multiple sclerosis, neuromyelitis optica, organ injury in patients undergoing cardiac surgery, ischemia-reperfusion associated injuries of the heart and lung, and osteoporosis.

According to one embodiments, the wound is in the skin of the subject.

According to one embodiment, the therapeutically acceptable amount is within a dosage range of 0.05-60 mg/kg.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this

BRIEF DESCRIPTION OF THE DRAWINGS

FIGS. 1A-G. Alpha 1 Antitrypsin. (1A) Computerized 3D model of AAT. Arrows, mutagenesis specific loci, $C^{232}$ and $P^{357}$. (1B) FASTA sequence of WT-hAAT and 3 generated mutations. Bold and underlined, mutation sites. (1C) Representative Commassie brilliant blue blot of purified rhAAT variants and serum purified hAAT. (1D) Computerized 3D model of AAT. Arrows, mutagenesis locus C232P and tryptophans W194 and W238. (1E) A line graph of fluorescent intensity from the tryptophans of WT-rhAAT and C232P-rhAAT. (1F) Line graph of inhibitory potency of WT-hAAT and serum-purified hAAT over neutrophil elastase. Grey, concentrations range used in this study. Triangle, concentration used in anti-inflammatory studies. Data representative of 3 independent experimental repeats. (1G) Line graph of fluorescence from a FRET substrate in the presence of proteinase 3 (PR3) with and without WT-rhAAT, serum-purified hAAT and CP-rhAAT.

DETAILED DESCRIPTION OF THE INVENTION

Figure 1E:
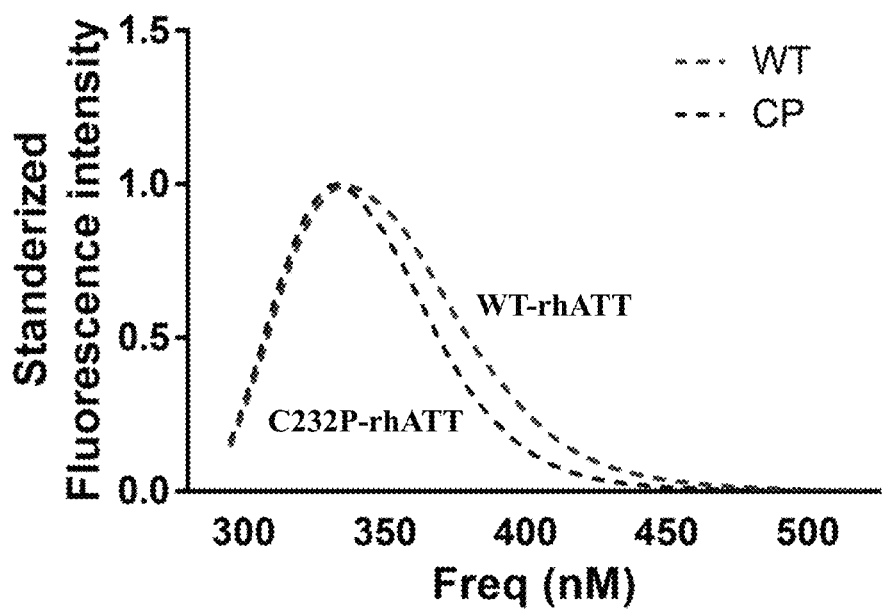

The present invention provides, in some embodiments, a mutant alpha 1-antitrypsin protein, a pharmaceutical composition comprising same and uses thereof.

By one aspect, the present invention provides an isolated polypeptide, comprising the following amino acid sequence: EDPQGDAAQKTDTSHHDQDHPTFNKITPNLAEFAFS-LYRQLAHQSNSTNIFFSPVSIATAF AMLSLGTKADTH-DEILEGLNFNLTEIPEAQI-HEGFQELLRTLNQPDSQLQLTTGNGLFLSE GLKLVDKFLEDVKKLYHSEAFTVNFGDTEEAKKQIN-DYVEKGTQGKIVDLVKELDRDT VFALVNYIFFKGK-WERPFEVKDTEEEDFHVDQVTTVKVPMMKRLGMF-NIQHXKKLSS WVLLMKYLGNATAIFFLPDEGKLQHLENELTHDI-ITKFLENEDRRSASLHLPKLSITGTY DLKSVLGQLGITKVFSNGADLSGVTEEAPLKL-SKAVHKAVLTIDEKGTEAAGAMFLEAI PMSIPPE-VKFNKPFVFLMIEQNTKSPLFMGKVVNPTQK (SEQ ID NO: 1), or a fragment, a derivative or analog thereof, wherein X is any amino acid other than cysteine or absent. In some embodiments, the amino acid is present and is any amino acid other than cysteine.

As used herein, the terms "peptide", "polypeptide" and "protein" are used interchangeably to refer to a polymer of amino acid residues. In some embodiment, the peptides, polypeptides and proteins described herein have modifications rendering them more stable while in the body, more capable of penetrating into cells or capable of eliciting a more potent effect than previously described. In some embodiment, the terms "peptide", "polypeptide" and "protein" apply to naturally occurring amino acid polymers. In another embodiment, the terms "peptide", "polypeptide" and "protein" apply to amino acid polymers in which one or more amino acid residue is an artificial chemical analogue of a corresponding naturally occurring amino acid.

As used herein, the term "isolated polypeptide" refers to a peptide that is essentially free from contaminating cellular components, such as carbohydrate, lipid, or other proteinaceous impurities associated with the peptide in nature. Typically, a preparation of isolated peptide contains the peptide in a highly-purified form, i.e., at least about 80% pure, at least about 90% pure, at least about 95% pure, greater than 95% pure, or greater than 99% pure. Each possibility represents a separate embodiment of the invention.

The term "fragment" as used herein, refers to a portion of the polypeptide, but a portion that still comprises the X found at position 232 of the sequence and wherein the X is any amino acid other than cysteine or is an absent amino acid. Such a fragment will still be recognizable as being from the polypeptide of the invention, and as such will be at least 10 amino acids in length. As such, any fragment of the isolated polypeptide of the invention will still comprise at least 10, at least 20, at least 30, at least 40, at least 50, at least 80, or at least 100 amino acids surrounding position 232. Each possibility represents a separate embodiment of the present invention.

The term "derivative" as used herein, refers to any polypeptide that is based off the polypeptide of the invention and still comprises the X found at position 232 of the sequence and wherein the X is any amino acid other than cysteine or is an absent amino acid. A derivative is not merely a fragment of the polypeptide, nor does it have amino acids replaced or removed (an analog), rather it may have additional modification made to the polypeptide, such as post-translational modification. Further, a derivative may be a derivative of a fragment of the polypeptide of the invention, however, in such a case the fragment must comprise at least 100 consecutive amino acids of the polypeptide of the invention.

The term "analog" as used herein, refers to a polypeptide that is similar, but not identical, to the polypeptide of the invention. An analog, may have deletions or mutations that result in an amino acids sequence that is different than the amino acid sequence of the polypeptide of the invention. It should be understood, that all analogs of the polypeptide of the invention would comprise the X at position 232; wherein the X is any amino acid other than cysteine or is an absent amino acid. Further, an analog may be analogous to a fragment of the polypeptide of the invention, however, in such a case the fragment must comprise at least 100 consecutive amino acids of the polypeptide of the invention.

In some embodiments, an analog to the polypeptide of the invention comprises an amino acid sequence with at least 60%, at least 65%, at least 70%, at least 75%, at least 80%, at least 85%, at least 90%, at least 95%, at least 99% homology to the following amino acid sequence EDPQGDAAQKTDTSHHDQDHPTFNKITPNLAEFAFS-LYRQLAHQSNSTNIFFSPVSIATAF AMLSLGTKADTH-DEILEGLNFNLTEIPEAQI-HEGFQELLRTLNQPDSQLQLTTGNGLFLSE GLKLVDKFLEDVKKLYHSEAFTVNFGDTEEAKKQIN-DYVEKGTQGKIVDLVKELDRDT VFALVNYIFFKGK-WERPFEVKDTEEEDFHVDQVTTVKVPMMKRLGMF-NIQHCKKLSS WVLLMKYLGNATAIFFLPDEGKLQHLENELTHDI-ITKFLENEDRRSASLHLPKLSITGTY DLKSVLGQLGITKVFSNGADLSGVTEEAPLKL-SKAVHKAVLTIDEKGTEAAGAMFLEAI PMSIPPE-VKFNKPFVFLMIEQNTKSPLFMGKVVNPTQK (SEQ ID NO: 2), and does not comprise a cysteine at position 232. Each possibility represents a separate embodiment of the present invention. In some embodiments, an analog to the polypeptide of the invention comprises an amino acid sequence with at least 70% homology to SEQ ID NO: 2.

In some embodiments, an analog to the polypeptide of the invention comprises an amino acid sequence with at least 60%, at least 65%, at least 70%, at least 75%, at least 80%, at least 85%, at least 90%, at least 95%, at least 99% homology to amino acid sequence set forth in SEQ ID NO: 1, and does not comprise a cysteine at position 232. Each possibility represents a separate embodiment of the present invention.

In some embodiments, an analog to the polypeptide of the invention has substantially the same tryptophan fluorescence intensity. In some embodiments, an analog to the polypeptide of the invention has a tryptophan fluorescence intensity not more than 1%, 2%, 3%, 4%, 5%, 10%, 15%, 20%, 25%, 30%, 35%, 40%, 45%, 50%, 55% or 60% more or less than the tryptophan fluorescence intensity of the polypeptide of the invention. Each possibility represents a separate embodiment of the invention.

In some embodiments, the amino acid sequence comprises the absence of an amino acid at position 232 of SEQ ID NO: 1. In some embodiments, the X in the polypeptide of the invention is an absent amino acid. In some embodiments, such a deletion or absence would entail deleting all three base pairs of the codon coding for an amino acid previously at position 232.

In some embodiments, the amino acid sequence comprises a mutation of the cysteine at position 232 of SEQ ID NO: 1. In some embodiments, the X in the polypeptide of the invention is selected from the group of amino acids consisting of: proline, valine, threonine, serine and isoleucine. In some embodiments, the X in the polypeptide of the invention is a proline. In some embodiments, the cysteine at position 232 of SEQ ID NO: 2 is mutated to a proline. Such a mutation would require changing at least each of the first two bases of the codon, from UG to CC.

In some embodiments, the amino acid sequence comprises the amino acid sequence set forth in SEQ ID NO: 1. In some embodiments, the amino acid sequence consists of the amino acid sequence set forth in SEQ ID NO: 1.

In some embodiments, the isolated polypeptides of the invention further comprise a mutation at position 357, wherein a proline at position 357 is mutated to any amino acid other than proline or an absent amino acid. In some embodiments, the proline is mutated to an amino acid selected from the group consisting of: cysteine, alanine, methionine, isoleucine, and valine. In some embodiments, the proline is mutated to an absent amino acid. In some embodiments, the proline is mutated to an amino acid selected from cysteine and alanine. In some embodiments, the proline is mutated to cysteine. Such a mutation would require changing at least the first two bases of a codon, from CC to UG and possibly also changing the third base to U or C. In some embodiments, the proline is mutated to alanine. Such a mutation would require changing at least the first base of a codon, from C to G.

Therapeutic Properties

In some embodiments, the isolated polypeptides of the invention have at least one therapeutic property that is greater than the same therapeutic property of recombinant human AAT (rhAAT) protein or serum purified hAAT. In some embodiments, the isolated polypeptides of the invention have at least one therapeutic property that is greater than the same therapeutic property of a polypeptide comprising an amino acid sequence with at least 70% homology to SEQ ID NO: 2. In some embodiments, the isolated polypeptides of the invention have at least one therapeutic property that is greater than the same therapeutic property of recombinant human AAT (rhAAT) protein. In some embodiments, the isolated polypeptides of the invention have at least one therapeutic property that is greater than the same therapeutic property of serum purified hAAT.

A "therapeutic property", as used herein, refers to any measurable way in which a protein exerts a therapeutic result on a subject, including on any disease, condition, disorder, damage or another non-optimal physical condition. In some embodiments, the therapeutic property is a therapeutic benefit.

In some embodiments, the therapeutic property is selected from an anti-inflammatory property and a wound healing property. In some embodiments, the therapeutic property is an anti-inflammatory property. In some embodiments, the therapeutic property is a wound healing property. In some embodiments, the therapeutic property is an anti-inflammatory property and/or a wound healing property.

In some embodiments, the isolated polypeptides of the invention have at least one anti-inflammatory property that is greater than the same anti-inflammatory property of recombinant human AAT (rhAAT) protein or serum purified hAAT. In some embodiments, the isolated polypeptides of the invention have at least one anti-inflammatory property that is greater than the same anti-inflammatory property of a polypeptide comprising an amino acid sequence with at least 70% homology to SEQ ID NO: 2. In some embodiments, the isolated polypeptides of the invention have at least one anti-inflammatory property that is greater than the same anti-inflammatory property of recombinant human AAT (rhAAT) protein. In some embodiments, the isolated polypeptides of the invention have at least one anti-inflammatory property that is greater than the same anti-inflammatory property of serum purified hAAT.

The amino acid sequence set forth in SEQ ID NO:2 codes for the hAAT. Alpha 1-antitrypsin is a known anti-inflammatory protein. An "anti-inflammatory property", as used herein, refers to any measurable way in which an anti-inflammatory protein exerts its anti-inflammatory effect. In some embodiments, the anti-inflammatory property is selected from the group consisting of: reducing secretion of a pro-inflammatory cytokine and reducing activation of macrophages. In some embodiments, the anti-inflammatory property is reducing secretion of an inflammatory cytokine. In some embodiments, the anti-inflammatory property is reducing activation of macrophages.

In some embodiments, reducing secretion of a pro-inflammatory cytokine is reducing secretion as by 10%, 20%, 30%, 40%, 50%, 60%, 70%, 80%, 90%, 95%, or 99%. Each possibility is a separate embodiment of the invention.

In some embodiments, reducing activation of macrophages is reducing the number of activated macrophages in a sample by 10%, 20%, 30%, 40%, 50%, 60%, 70%, 80%, 90%, 95%, or 99%. Each possibility is a separate embodiment of the invention. In some embodiments, reducing activation of macrophages is reducing the macrophage cell surface expression of a co-stimulatory molecule by 10%, 20%, 30%, 40%, 50%, 60%, 70%, 80%, 90%, 95%, or 99%. Each possibility is a separate embodiment of the invention.

Pro-inflammatory cytokines are well known in the art and are sometimes also referred to as inflammatory cytokines. A cytokine is a substance secreted by cells that has effects on other cells. In this instance, the effect is inducing inflammation. Pro-inflammatory cytokines include, but are not limited to, IL-1, IL-12, TNF-α, IL-8, MCP1, IL-18 and INFγ. In some embodiments, the pro-inflammatory cytokines are selected from the group consisting of IL-6 and TNF-α.

During inflammation, immune cells respond to the cite of inflammation. Macrophages, specifically, become activated and increase synthesis of enzymes and other active proteins. Macrophage activation is facilitated by co-stimulatory molecules on the macrophages cell surface. Reduction of the surface expression of this co-stimulatory molecule results in reduced activation of the macrophage. A reduction in the percent of macrophages that expresses these molecules will result in a lower percentage of the macrophage population becoming stimulated. In some embodiments, reducing activation of macrophages comprises reducing cell surface expression of a co-stimulatory molecule. In some embodiments, the co-stimulatory molecule is selected from the group consisting of: CD40 and CD86.

In some embodiments, the isolated polypeptides of the invention have at least one wound healing property that is greater than the same wound healing property of recombinant human AAT (rhAAT) protein or serum purified hAAT. In some embodiments, the isolated polypeptides of the invention have at least one wound healing property that is greater than the same wound healing property of a polypeptide comprising an amino acid sequence with at least 70% homology to SEQ ID NO: 2. In some embodiments, the isolated polypeptides of the invention have at least one wound healing property that is greater than the same wound healing property of recombinant human AAT (rhAAT) protein. In some embodiments, the isolated polypeptides of the invention have at least one wound healing property that is greater than the same wound healing property of serum purified hAAT.

The amino acid sequence set forth in SEQ ID NO:2 codes for the hAAT. Alpha 1-antitrypsin is a known inducer of wound healing. A "wound healing property", as used herein, refers to any measurable way in which a protein exerts a pro healing effect on a wound. As used herein, a "wound" refers to wound, physical damage or incision that occurs to a tissue of an organism. A wound may refer to any wound, at any stage of the healing process, including the stage before healing has begun. In some embodiments, the wound is an external wound. In some embodiments, the wound is an internal wound. In some embodiments, the wound is a wound to the skin. In some embodiments, the wound is a surgical wound. In some embodiments, the wound healing property is selected from the group consisting of: increasing the rate of wound healing, increasing the rate of wound closure, and inducing wound closure/healing to begin sooner. In some embodiments, the wound healing property is increasing the rate of wound closure and/or healing. In some embodiments, the wound healing property is inducing wound closure to begin sooner. In some embodiments, inducing wound closure to begin sooner comprises decreasing the lag until the onset of wound healing.

Examples of wounds which can be prevented and/or treated in accordance with the present invention are, e.g., aseptic wounds, contused wounds, incised wounds, lacerated wounds, non-penetrating wounds (i.e. wounds in which there is no disruption of the skin but there is injury to underlying structures), open wounds, penetrating wound, perforating wounds, puncture wounds, septic wounds, subcutaneous wounds, etc. Examples of sores are bed sores, canker sores, chrome sores, cold sores, pressure sores etc.

Examples of ulcers are, e.g., peptic ulcer, duodenal ulcer, gastric ulcer, gouty ulcer, diabetic ulcer, hypertensive ischemic ulcer, stasis ulcer, ulcus cruris (venous ulcer), sublingual ulcer, submocous clear, symptomatic ulcer, trophic ulcer, tropical ulcer, veneral ulcer, e.g. caused by gonorrhoea (including urethritis, endocervicitis and proctitis). Conditions related to wounds or sores which may be successfully treated according to the invention are burns, anthrax, tetanus, gas gangrene, scalatina, erysipelas, sycosis barbae, folliculitis, impetigo contagiosa, or impetigo bullosa, etc. There is often a certain overlap between the use of the terms "wound" and "ulcer" and "wound" and "sore" and, furthermore, the terms are often used at random. Therefore, as mentioned above, in the present context the term "wound" encompasses the term "ulcer", "lesion", "sore" and "infarction", and the terms are indiscriminately used unless otherwise indicated.

The kinds of wounds to be treated according to the invention include also i) general wounds such as, e.g., surgical, traumatic, infectious, ischemic, thermal, chemical and bullous wounds; ii) wounds specific for the oral cavity such as, e.g., post-extraction wounds, endodontic wounds especially in connection with treatment of cysts and abscesses, ulcers and lesions of bacterial, viral or autoimmunological origin, mechanical, chemical, thermal, infectious and lichenoid wounds; herpes ulcers, stomatitis aphthosa, acute necrotising ulcerative gingivitis and burning mouth syndrome are specific examples; and iii) wounds on the skin such as, e.g., neoplasm, burns (e.g. chemical, thermal), lesions (bacterial, viral, autoimmunological), bites and surgical incisions. Another way of classifying wounds is as i) small tissue loss due to surgical incisions, minor abrasions and minor bites, or as ii) significant loss. The latter group includes ischemic ulcers, pressure sores, fistulae, lacerations, severe bites, thermal burns and donor site wounds (in soft and hard tissues) and infarctions.

In some embodiments, increasing the rate of wound healing/closure is increasing the rate by at least 10%, 20%, 30%, 40%, 50%, 60%, 70%, 80%, 90%, 95%, 100%, 150%, 200%, 250%, 300%, 350%, 400%, 450%, 500%, 600%, 700%, 800%, 900%, or 1000%. Each possibility is a separate embodiment of the invention.

In some embodiments, decreasing the lag until the onset of wound healing/closure is decreasing the time until the onset of wound healing/closure by at least 10%, 20%, 30%, 40%, 50%, 60%, 70%, 80%, 90%, 95%, 97% or 99%. Each possibility is a separate embodiment of the invention. In some embodiments, the time until the onset of wound healing/closure is decreased by at least 30 minutes, 1 hour, 2 hours, 3 hours, 4 hours, 5 hours, 6 hours, 7 hours, 8 hours, 9 hours, 10 hours, 11 hours, 12 hours, 16 hours, 20 hours or 24 hours. Each possibility is a separate embodiment of the invention.

As used herein, the term "recombinant protein" refers to protein which is coded for by a recombinant DNA and is thus not naturally occurring. In some embodiments, the isolated polypeptide is a recombinant protein. In some embodiments, the isolated polypeptide is rhAAT. The term "recombinant DNA" refers to DNA molecules formed by laboratory methods of genetic recombination. Generally, this recombinant DNA is in the form of a vector used to express the recombinant protein in a cell.

In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid" which refers to a circular double stranded DNA loop into which additional DNA segments can be inserted, such as by standard molecular cloning techniques. Another type of vector, wherein virally-derived DNA or RNA sequences are present in the virus (e.g. retroviruses, replication defective retroviruses, adenoviruses, replication defective adenoviruses, and adeno-associated viruses). Viral vectors also include polynucleotides carried by a virus for transfecting into host cells. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". Common expression vectors of utility in recombinant DNA techniques are often in the form of plasmids.

Recombinant expression vectors can comprise a nucleic acid coding for the protein of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

A vector nucleic acid sequence generally contains at least an origin of replication for propagation in a cell and optionally additional elements, such as a heterologous polynucleotide sequence, expression control element (e.g., a promoter, enhancer), selectable marker (e.g., antibiotic resistance), poly-Adenine sequence.

The vector may be a DNA plasmid delivered via non-viral methods or via viral methods. The viral vector may be a retroviral vector, a herpesviral vector, an adenoviral vector, an adeno-associated viral vector or a poxviral vector. The promoters may be active in mammalian cells. The promoters may be a viral promoter.

In some embodiments, the vector is introduced into the cell by standard methods including electroporation (e.g., as described in From et al., Proc. Natl. Acad. Sci. USA 82, 5824 (1985)), heat shock, infection by viral vectors, high velocity ballistic penetration by small particles with the nucleic acid either within the matrix of small beads or particles, or on the surface (Klein et al., Nature 327. 70-73 (1987)), and/or the like.

General methods in molecular and cellular biochemistry, such as may be useful for carrying out DNA and protein recombination, as well as other techniques described herein, can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al.

eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998).

It should be well understood to a person of skill in the art that a recombinant protein is produced by expressing the recombinant DNA in a cell and then purifying the protein. The cells expressing the DNA are cultured under effective conditions, which allow for the expression of high amounts of recombinant polypeptide. Such effective culture conditions include, but are not limited to, effective media, bioreactor, temperature, pH and oxygen conditions that permit protein production. In one embodiment, an effective medium refers to any medium in which a cell is cultured to produce the recombinant polypeptide of the present invention. In some embodiments, a medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

Purification of a recombinant protein involves standard laboratory techniques for extracting a recombinant protein that is essentially free from contaminating cellular components, such as carbohydrate, lipid, or other proteinaceous impurities associated with the peptide in nature. Purification can be carried out using a tag that is part of the recombinant protein or thought immuno-purification with antibodies directed to the recombinant protein. Kits are commercially available for such purifications and will be familiar to one skilled in the art. Typically, a preparation of purified peptide contains the peptide in a highly-purified form, i.e., at least about 80% pure, at least about 90% pure, at least about 95% pure, greater than 95% pure, or greater than 99% pure. Each possibility represents a separate embodiment of the invention.

Mutations and deletions in a protein are created by introducing the mutation or deletion into the coding DNA. Methods of site-directed mutagenesis, and routine DNA recombination can be found in such standard textbooks as are enumerated above. Mutagenesis of one amino acid to another may require mutation of 1, 2, or 3 of the bases that make up the codon corresponding to the amino acid to be changed.

Pharmacokinetics

In some embodiments, the polypeptides of the invention are pharmacokinetically advantageous as compared to rhAAT protein or serum purified hAAT. In some embodiments, the polypeptides of the invention are pharmacokinetically advantageous as compared to a polypeptide comprising an amino acid sequence with at least 70% homology to SEQ ID NO: 2. In some embodiments, the polypeptides of the invention are pharmacokinetically advantageous as compared to rhAAT protein. In some embodiments, the polypeptides of the invention are pharmacokinetically advantageous as compared to serum purified hAAT.

The term "pharmacokinetics" and "pharmacokinetically" refer to the chemical metabolism of the protein within a subject. That is, the stability, distribution, and longevity of the protein from its administration to a subject, until it is completely eliminated from the subject's body. In some embodiments, the subject who receives the protein is a mammal. In some embodiments, the subject is a model laboratory animal, such as a mouse, rat or monkey. In some embodiments, the subject is a human.

Greater pharmacokinetic utility, that is a protein that is pharmacokinetically advantageous, will induce a greater biological response as compared to a different protein administered at the same dose, or, at a reduced dose, will induce the same biological response as a different protein.

In some embodiments, pharmacokinetic utility will be increased if a protein is one of the following relative to a different protein: more stable within a subject, distributes better throughout the body of a subject, has greater bioavailability within a subject, or survives longer within a subject without being metabolized. In some embodiments, a pharmacokinetically advantageous polypeptide comprises one or more properties selected from: increased serum stability, increased distribution, and increased bioavailability.

The term "bioavailability" as used herein refers to the proportion of the protein that enters the blood stream and is thus able to exert a biological effect. When a protein is administered intravenously the bioavailability is 100%, however, different methods of administration will result in different bioavailability and will be dependent on the specific composition of the protein being administered.

In some embodiments, pharmacokinetic utility is determined by measuring at least one parameter selected from the group consisting of: serum concentration after dosing, distribution volume, and half-life.

Serum concentration refers to the concentration of the protein within the bloodstream of the subject. This can be calculated by drawing blood from the subject and measuring how much of the protein is present. In some embodiments, concentrations are tested multiple times after the protein is administered. In some embodiments, the concentration is tested every hour after administration. In some embodiments, the concentration is tested after one hour, after two hours, after three hours, after four hours, after five hours, after six hours, after twelve hours and after twenty-four hours. In some embodiments, testing is only performed for up to one day after administration. In some embodiments, absolute levels of the protein are used to calculate pharmacokinetic stability. In some embodiments, percent of the protein remaining relative to peak concentrations (immediately after dosing) is used to calculate pharmacokinetic stability.

A decrease in serum concentration over time is to be expected as the protein is metabolized. In some embodiments, a slower rate of decrease indicates greater stability of the protein and is pharmacokinetically advantageous. In some embodiments, a slower rate of decrease indicates an alteration in the distribution volume quality of the protein which is pharmacokinetically advantageous. When a protein is administered intravenously, 100% of it reaches the bloodstream, and as such bioavailability of all administered proteins will be the same. Thus, a significantly lower serum concentration shortly after dosing indicates that the protein has better left the bloodstream and been better distributed to the tissues of the body. In some embodiments, this increased distribution is pharmacokinetically advantageous as more drug will reach the site at which it can act, or alternatively a lower dose can be administered in order for the same amount of protein to reach the site of action. In some embodiments, this increased distribution is pharmacokinetically advantageous as less drug is available for serum elimination in designated organs such as the liver or the kidney, thus prolonging the temporal length of its effect. In some embodiments, such a decrease is measured after 30 minutes, after 1 hour, after 2 hours, after 3 hours, after 4 hours, after 5 hours or after 6 hours. Each possibility represents a separate embodiment of the present invention. In some embodiments, the decrease is measured at any time after administration.

In some embodiments, any decrease in serum concentration as compared to another protein is pharmacokinetically advantageous. In some embodiments, at least a 1%, at least a 5%, at least a 10%, at least a 15%, at least a 20%, at least a 25%, at least a 30% at least a 35%, at least a 40%, at least a 45%, at least a 50%, at least a 55%, at least a 60%, at least a 65%, at least a 70%, at least a 75%, at least a 80%, at least a 85%, at least a 90%, at least a 95%, at least a 100%, at least a 150%, at least a 200%, at least a 250%, at least a 300%, at least a 350%, at least a 400%, at least a 450%, at least a 500%, at least a 550%, at least a 600%, at least a 650%, at least a 700%, or at least a 750% decrease in serum concentration as compared to another protein is pharmacokinetically advantageous. Each possibility represents a separate embodiment of the present invention. In some embodiments, at least a 1-fold, at least a 2-fold, at least a 3-fold, at least a 4-fold, at least a 5-fold, at least a 6-fold, at least a 7-fold or at least an 8-fold decrease in serum concentration as compared to another protein is pharmacokinetically advantageous. Each possibility represents a separate embodiment of the present invention.

The term "distribution volume" as used herein refers to the theoretical volume that would be needed to contain all of the administered protein such that it would have the observed concentration in the blood. That is, if two drugs are administered at the same dose, but one has a serum concentration that is half of the other, then it has a distribution volume that is twice the other. A higher distribution volume, means that a protein is more distributed throughout the body, and less present in the bloodstream. The formula for calculating distribution volume is:

$$V_D = \text{total drug administered/drug serum concentration}$$

In some embodiments, any increase in distribution volume as compared to another protein is pharmacokinetically advantageous. In some embodiments, at least a 1%, at least a 5%, at least a 10%, at least a 15%, at least a 20%, at least a 25%, at least a 30% at least a 35%, at least a 40%, at least a 45%, at least a 50%, at least a 55%, at least a 60%, at least a 65%, at least a 70%, at least a 75%, at least a 80%, at least a 85%, at least a 90%, at least a 95%, at least a 100%, at least a 150%, at least a 200%, at least a 250%, at least a 300%, at least a 350%, at least a 400%, at least a 450%, at least a 500%, at least a 550%, at least a 600%, at least a 650%, at least a 700%, or at least a 750% increase in distribution volume as compared to another protein is pharmacokinetically advantageous. Each possibility represents a separate embodiment of the present invention. In some embodiments, at least a 1-fold, at least a 2-fold, at least a 3-fold, at least a 4-fold, at least a 5-fold, at least a 6-fold, at least a 7-fold or at least an 8-fold increase in distribution volume as compared to another protein is pharmacokinetically advantageous. Each possibility represents a separate embodiment of the present invention.

In some embodiments, the term "half-life" as used herein refers to the time it takes for the protein within the body of a subject to reduce to half its initial amount. In some embodiments, the term "half-life" refers to the time it takes for the protein within the blood to reduce to have its initial concentration. In some embodiments, the term "half-life" refers to the time it takes for the protein within the body of a subject to reduce to half of its pharmacologic activity. A longer half-life means the protein is staying biologically active and present in the subject for a longer time. In. some embodiments, the formula used to calculate half-life of the protein is:

$$T_{1/2} = ln2 * V_D/CL$$

In some embodiments, any increase in half-life as compared to another protein is pharmacokinetically advantageous. In some embodiments, at least a 1%, at least a 5%, at least a 10%, a at least 15%, at least a 20%, at least a 25%, at least a 30% at least a 35%, at least a 40%, at least a 45%, at least a 50%, at least a 55%, at least a 60%, at least a 65%, at least a 70%, at least a 75%, at least a 80%, at least a 85%, at least a 90%, at least a 95%, at least a 100%, at least a 150%, at least a 200%, at least a 250%, at least a 300%, at least a 350%, at least a 400%, at least a 450%, at least a 500%, at least a 550%, at least a 600%, at least a 650%, at least a 700%, or at least a 750% increase in half-life as compared to another protein is pharmacokinetically advantageous. Each possibility represents a separate embodiment of the present invention. In some embodiments, at least a 1-fold, at least a 2-fold, at least a 3-fold, at least a 4-fold, at least a 5-fold, at least a 6-fold, at least a 7-fold or at least an 8-fold increase in half-life as compared to another protein is pharmacokinetically advantageous. Each possibility represents a separate embodiment of the present invention.

Pharmaceutical Compositions

By another aspect, there is provided a pharmaceutical composition comprising any of the isolated polypeptides of the invention and a pharmaceutically acceptable carrier, excipient, or adjuvant.

As used herein, the term "carrier," or "excipient" refers to any component of a pharmaceutical composition that is not the active agent. As used herein, the term "pharmaceutically acceptable carrier" refers to non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations. Some non-limiting examples of substances which can serve as a carrier herein include sugar, starch, cellulose and its derivatives, powered tragacanth, malt, gelatin, talc, stearic acid, magnesium stearate, calcium sulfate, vegetable oils, polyols, alginic acid, pyrogen-free water, isotonic saline, phosphate buffer solutions, cocoa butter (suppository base), emulsifier as well as other non-toxic pharmaceutically compatible substances used in other pharmaceutical formulations. Wetting agents and lubricants such as sodium lauryl sulfate, as well as coloring agents, flavoring agents, excipients, stabilizers, antioxidants, and preservatives may also be present. Any non-toxic, inert, and effective carrier may be used to formulate the compositions contemplated herein. Suitable pharmaceutically acceptable carriers, excipients, and diluents in this regard are well known to those of skill in the art, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide," U.S. Food and Drug Administration (FDA) Center for Drug Evaluation and Research (CDER) Office of Management, the contents of all of which are hereby incorporated by reference in their entirety. Examples of pharmaceutically acceptable excipients, carriers and diluents useful in the present compositions include distilled water, physiological saline, Ringer's solution, dextrose solution, Hank's solution, and DMSO. These additional inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990); Remington's Pharmaceutical Sciences, 18th Ed., Mack Publishing Co., Easton, Pa. (1990); and Remington: The Science and Practice of Pharmacy, 21st Ed., Lippincott Williams & Wilkins, Philadelphia, Pa., (2005), each of which is incorporated by reference herein in its entirety. The presently described composition may also be contained in artificially created structures such as liposomes, ISCOMS, slow-releasing particles, and other vehicles which increase the half-life of the peptides or polypeptides in serum. Liposomes include emulsions, foams, micelies, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, Current Protocols in Protein Science, 1999, John Wiley & Sons, Inc., New York, and see also U.S. Pat. Nos. 4,235,871, 4,501,728, 4,837,028, and 5,019,369.

The carrier may comprise, in total, from about 0.1% to about 99.99999% by weight of the pharmaceutical compositions presented herein.

The pharmaceutical composition may take any physical form necessary for proper administration. The composition may be administered orally in the form of a pill, capsule or liquid. The composition may be in the form of a gel, spray, cream or ointment.

Therapeutic Use

By another aspect, there is provided a method of treating a subject in need of alpha 1-antitrypsin therapy, the method comprising administering to the subject a therapeutically effective amount of any of the above described pharmaceutically compositions, thereby treating a subject in need of alpha 1-antitrypsin therapy.

By another aspect, there is provided use of a pharmaceutical composition of the invention to treat a subject in need of alpha 1-antitrypsin therapy.

In some embodiments, the subject in need of alpha 1-antitrypsin therapy has an alpha 1-antitrypsin deficiency.

In some embodiments, a subject in need of alpha 1-antitrypsin therapy is a subject with an inflammatory disease, disorder or condition. In some embodiments, a subject in need of alpha 1-antitrypsin therapy is a subject with a disease, disorder or condition of the immune system. In some embodiments, a subject in need of alpha 1-antitrypsin therapy is a subject with a disease, disorder or condition characterized by cellular necrosis. In some embodiments, a subject in need of alpha 1-antitrypsin therapy is a subject with a wound.

In some embodiments, a subject in need of alpha 1-antitrypsin therapy requires therapy for a disease, disorder or condition selected from the group consisting of: diabetes, allogenic and xenogeneic transplantation, graft-versus-host disease, myocardial infarction, radiation exposure, chronic fatigue syndrome, bacterial infection, inflammatory bowel disease, rheumatoid arthritis, liver disease, radiation exposure, osteoporosis, multiple sclerosis, neuromyelitis optica, organ injury in patients undergoing cardiac surgery, ischemia-reperfusion associated injuries of the heart and lung, an external wound, an internal wound, skin necrosis, skin damage and osteoporosis.

By another aspect, there is provided a method of treating, ameliorating or preventing an inflammatory disease or disorder in a subject in need thereof, the method comprising administering to the subject a therapeutically effective amount of any of the above described pharmaceutically compositions, thereby treating, ameliorating or preventing the inflammatory disease or disorder in said subject.

By another aspect, there is provided use of a pharmaceutical composition of the invention to treat, ameliorate or prevent and inflammatory disease or disorder in a subject in need thereof.

In some embodiments, the inflammatory-associated disease or disorder has an immune system component. In some embodiments, the disease or disorder with an immune system component is selected from the group consisting of: diabetes, allogenic and xenogeneic transplantation, graft-versus-host disease, bacterial infection, rheumatoid arthritis, inflammatory bowel disease, osteoarthritis, vasculitis, chronic fatigue syndrome and multiple sclerosis. In some embodiments, the inflammatory-associated disease or disorder has a necrotic component. In some embodiments, the disease or disorder with a necrotic component is selected from the group consisting of: myocardial infarction, radiation exposure, and liver disease.

In some embodiments, the inflammatory disease or disorder is selected from the group consisting of: diabetes, diabetes, allogenic and xenogeneic transplantation, graft-versus-host disease, myocardial infarction, radiation exposure, chronic fatigue syndrome, bacterial infection, inflammatory bowel disease, rheumatoid arthritis, liver disease, radiation exposure, osteoporosis, multiple sclerosis, neuromyelitis optica, organ injury in patients undergoing cardiac surgery, ischemia-reperfusion associated injuries of the heart and lung, and osteoporosis.

By another aspect, there is provided a method of treating a wound in a subject in need thereof, the method comprising administering to the subject a therapeutically effective amount of any of the above described pharmaceutically compositions, thereby treating the wound in said subject.

By another aspect, there is provided use of a pharmaceutical composition of the invention to treat a wound in a subject in need thereof.

In some embodiments, the wound is an external wound. In some embodiments, the wound is an internal wound. In some embodiments, the wound is a skin wound. In some embodiments, the wound is a result of surgery. In some embodiments, the wound has not yet begun to heal. In some embodiments, the pharmaceutical composition is provided prophylactically before the wound occurs.

As used herein, the terms "administering," "administration," and like terms refer to any method which, in sound medical practice, delivers a composition containing an active agent to a subject in such a manner as to provide a therapeutic effect. One aspect of the present subject matter provides for dermal or transdermal administration of a therapeutically effective amount of a composition of the present subject matter to a patient in need thereof. Other suitable routes of administration can include oral, dermal, transdermal, parenteral, subcutaneous, intravenous, intramuscular, or intraperitoneal. In some embodiments, the administering is systemic administering. In some embodiments, the administering to the wound. In some embodiments, the administering is to the site of inflammation.

Administering the composition to a specific site in the subject may be performed with any method known in the art. This may include with an applicator, in the form of a gel or cream, as well as on a scaffold, wrap or bandage.

In some embodiments, the pharmaceutical composition comprises protein in a dosage range of 0.05-60 mg/kg. In some embodiments, the pharmaceutical composition comprises protein in a dosage range of 0.05-60, 0.05-50, 0.05-40, 0.05-30, 0.05-20, 0.05-10, 0.05-5, 0.1-60, 0.1-50, 0.1-40, 0.1-30, 0.1-20, 0.1-10, 0.1-5, 0.5-60, 0.5-50, 0.5-40, 0.5-30, 0.5-20, 0.5-10, 0.5-5, 0.75-60, 0.75-50, 0.75-40, 0.75-30, 0.75-20, 0.75-10, 0.75-5, 1-60, 1-50, 1-40, 1-30, 1-20, 1-10, or 1-5 mg/kg. Each possibility represents a separate embodiment of the present invention.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

EXAMPLES

Materials and Methods

Plasmid Constructs

A human AAT EST clone was purchased from Open Biosystems (GE Healthcare, Chicago, Ill., USA) and amplified by PCR using FW 5'-GATCACCG-GTGAATTCGA-TATCTCGAGCACCATGGT-TATGCCGTCTTCTGTCTCGTGGGGCATCC-3' (SEQ ID NO: 3) and RE 5'-GCTGGGCAAGGTGGGCACTC-CACAGATCTCTACTA-GTGATGGTGATGATGATGAT-GATGTTTTTGGGTGGGATTCACCAC-3' (SEQ ID NO: 4) primers. A His-tag sequence was added C terminal of the resulting DNA. Specific mutations for the replacement of C232 and P357 were inserted by assembly PCR using the primers: For C232P: FW 5'-TTTAGGCATGTTTAA-CATCCAGCACCC-CAAGAAGCTGTCCAGCTGGGTGCTGCTG-3' (SEQ ID NO: 5) and RE 5'-GTGCTGGATGTTAAA-CATGCCTAAACG-3' (SEQ ID NO: 6). For P357C: FW 5'-TTAGAGGCCATATGCATGTCTATCCCCCCCGAGG-3' (SEQ ID NO: 7) and RE-5'CCTCGGGGGGGATAGA-CATGCATATGGCCTCTAA-3' (SEQ ID NO: 8). For P357A: FW 5'-GTTTTTAGAGGCCATAGCCATGTC-TATCCCCCCCGAG-3' (SEQ ID NO: 9) and RE 5'-CTCGGGGGGGATAGACATGGC-TATGGCCTCTAAAAAC-3' (SEQ ID NO: 10). Sequences were cloned into pFUSE plasmid (Invivogen, San Diego, Calif., USA) using NEBuilder HiFi DNA Assembly Master Mix (New England Biolabs, Ipswich, Mass., USA), according to manufacturer's instructions. Naïve human AAT signal peptide was used in protein expression. Plasmids were replicated in E. coli (HIT Competent Cells-DH5α, Real Biotech Corporation, Banqiao city, Taiwan) and purified using Wizard® Plus SV Minipreps DNA Purification Systems (Promega, Fitchburg, Wis., USA), according to manufacturer's instructions.

Recombinant Protein Production and Purification

HEK-293F cells (CRL-1573, ATCC, Manassas, W. Va., USA) were cultured in FreeStyle 293 expression medium (Invitrogen, Carlsbad, Calif., USA) in 8% $CO_2$ shaking incubator. Cells were transfected using GeneTran™ transfection reagent (Biomega, San Diego, Calif., USA) according to manufacturer's instructions. Six days post-transfection, supernatants were collected and secreted hAAT was purified using Ni beads (Calbiochem, Merck Millipore, Darmstadt, Germany) by standard protocol. After protein purification, samples were assessed for purity and molecular weight on a 10% polyacrylamide gel stained with coomassie brilliant blue reagent; commercial clinical-grade serum-purified hAAT (Glassia, Kamada, Ness-Ziona, Israel) was used as reference. Protein concentrations were determined using micro-volume spectrophotometer (Nanodrop, ThemoFisher Scientific, Waltham, Mass., USA) and Bradford Protein Assay (Bio-Rad Laboratories, Rishon-LeZion, Israel).

Neutrophil Elastase Activity Assay

Neutrophil elastase activity was determined in acellular conditions using a designated kit (R&D Systems, Minneapolis, Minn., USA), according to manufacturer's instruction. hAAT variants were pre-incubated with the enzyme prior to kinetic evaluation of substrate processing.

Mice

C57BL/6 mice (6-8 weeks old males and females from Harlan Laboratories LTD, Jerusalem, Israel) were used for all experiments. The study was approved by the Ben-Gurion University of the Negev animal care and use committee.

Production of Bone-Marrow-Derived Macrophages (BMDMs)

The tibia and femur of C57BL/6 mice were surgically removed and thoroughly flushed through a 70-µM sterile nylon cell strainer (Falcon; BD Biosciences Discovery Labware, San Jose, Calif., USA) with PBS (Biological Industries, Beit Ha'emek, Israel). Cells were resuspended and cultured in 10 ml complete RPMI-1640 (containing 10% fetal bovine serum, 50 U/ml streptomycin/penicillin, 50 µg/ml L-glutamine, all from Biological Industries), 50 µM β32-mercaptoethanol (Sigma-Aldrich, Rehovot, Israel) and 20 ng/ml recombinant Granulocyte Macrophage Colony-Stimulating Factor (rGM-CSF, PeproTech, Rocky Hill, N.J., USA). Fresh medium containing rGM-CSF was added on day 3 and on day 6. Cell populations were confirmed as being >95% $CD11b^{+\ after}$ 9 days of incubation with rGM-CSF.

Thioglycolate-Elicited Primary Peritoneal Macrophages

C57BL/6 mice were injected with thioglycolate (3% v/v, Sigma-Aldrich; i.p., 1.5 ml per mouse). Five days later, peritoneal lavage was performed with cold PBS. Recovered cell suspensions were filtered through a 70 µM sterile nylon strainer. Cells were then re-suspended in complete RPMI 1640. Cell cultures were routinely verified to be >95% $CD11b^+/F4-80^+$ cells.

Cell Activation Assays and Flow Cytometry

Peritoneal macrophages or BMDMs, as indicated, were seeded at $2-3 \times 10^5$ cells per well in 300 µl complete RPMI 1640. Recombinant hAAT variants were added at indicated concentrations for overnight incubation. Cells were then carefully washed with PBS and medium replaced with identical concentrations of hAAT variants as well as LPS (Sigma-Aldrich) at indicated concentrations. Twenty-four hours later supernatants were collected and analyzed for IL-6 and TNFα using specific ELISA (Biolegend, San Diego, Calif., USA)

Cells were gently removed with a rubber policeman and suspended in FACS buffer (PBS containing 1% BSA from Biological Industries, 0.1% sodium azide and 2 mM EDTA both from Sigma-Aldrich). Blocking was performed at room temperature for 20 minutes using anti-CD16/32 (Biolegend). Staining was performed at 4° C. for an additional 20 minutes using the following anti-mouse antibodies: anti-CD40-FITC (3/2.3), anti-CD86-PE (GL-1), anti-TNFα-APC (MP6-XT22), anti-CD11b-Pacific blue (M1/70), all from Biolegend, and anti-F4/80-PerCP-Cy5.5 (BM8.1) (Merc, Temecula, Calif., USA). Fluorescent readout was determined using BD Canto II and data were analyzed by FLOWJO 10.0.8r1 software (Flowjo, LLC Data Analysis Software, Ashland, Oreg., USA). In gating for BMDMs, CD11b and F4-80 double positive cells were selected.

In Vivo LPS-Induced Peritonitis

Mice were pretreated with equivalent volumes of PBS or rAAT (50 µg per mouse i.p., n=20 per experiment) for 3 hours, then treated with 1 mg/kg LPS (Sigma-Aldrich; i.p.). Blood samples (20 µl) were collected from the tail vein 1.5, 3 and 24 hours later, and separated by centrifuge; sera were analyzed for TNFα levels with specific ELISA (R&D Systems).

Real-Time Quantitative PCR

RAW264.7 cells (TIB-71, ATCC) were seeded at $5 \times 10^5$ cells per well in 500 µl of complete RPMI 1640. Cells were carefully washed, and medium replaced with identical concentrations of hAAT variants and LPS (Sigma-Aldrich) at indicated concentrations. Total RNA was purified at 1, 3 and 6 hours post stimulation using total RNA purification kit (Norgen, Thorold, Ontario, Canada), according to manufacturer's instructions. Sample concentrations were normalized to RNA content using micro-volume spectrophotometer (Nanodrop) and then reverse transcribed with qScript cDNA synthesis kit (Quanta Biosciences, Gaithersburg, Md., USA), according to manufacturer's instructions. cDNA amplification was performed, and gene transcription was analyzed quantitatively by real-time PCR (StepOnePlus real time PCR system, ThemoFisher Scientific) using the following primers (Sigma-Aldrich):

18S:
FW 5'-TCAACACAGGGATCGGACAACACA-3' (SEQ ID NO: 11)

RE 5'-GCCTTGGATCAAGTTCACAGGCAA-3'. (SEQ ID NO: 12)

TNFα:
FW 5'-CCCACGTCGTAGCAAACCAC-3' (SEQ ID NO: 13)

RE 5'-CCCTTGAAGAGAACCTGGGAG-3'. (SEQ ID NO: 14)

Pharmacokinetics Study

Mice were dosed intravenously (i.v) with indicated doses of recombinant hAAT variants. Blood samples (40 µl) were collected from the tail vein and circulating serum hAAT levels were determined at selected time-points using species-specific hAAT ELISA (ICL Lab, Portland, Oreg., USA). $T_{0.5}$ and distribution volume were calculated using PKsolver add-in for Microsoft Excel.

Statistical Analysis

Two-tailed Mann-Whitney test was used to assess differences between selected experimental conditions. Results are expressed as mean±SEM, p<0.05 was considered significant. All statistical analysis was performed using GraphPad Prism version 6.01.

Example 1: Recombinant hAAT Variants

Mutations at amino acid positions 357 (inside the reactive center loop, RCL) and 232 (outside the RCL) were generated, as depicted in FIGS. 1A and 1B; HEK-T293F cells were transfected with respective plasmid constructs and allowed to release His-tag WT recombinant hAAT (WT-rhAAT) and its variants (C232P, P357C and P357A). hAAT variants were then affinity-purified, and their size confirmed to be consistent with serum-purified commercially available clinical-grade human AAT (FIG. 1C).

Variant C232P was compared to WT rhAAT using tryptophan fluorescence spectroscopy in order to investigate if the mutation caused any conformational change to the protein. AAT contains two tryptophans, one at amino acid 194 and one at amino acid 238; thus, the mutation is made almost directly between the two residues (FIG. 1D). W194 is very highly conserved, with a consurf score of 9, while W238 is only mildly conserved with a consurf score of 5. When tryptophan fluorescence was measured the C232P mutant was found to be very minorly redshifted as compared to the WT, suggesting that the mutation caused a very small conformational change (FIG. 1E).

Figure 1F:
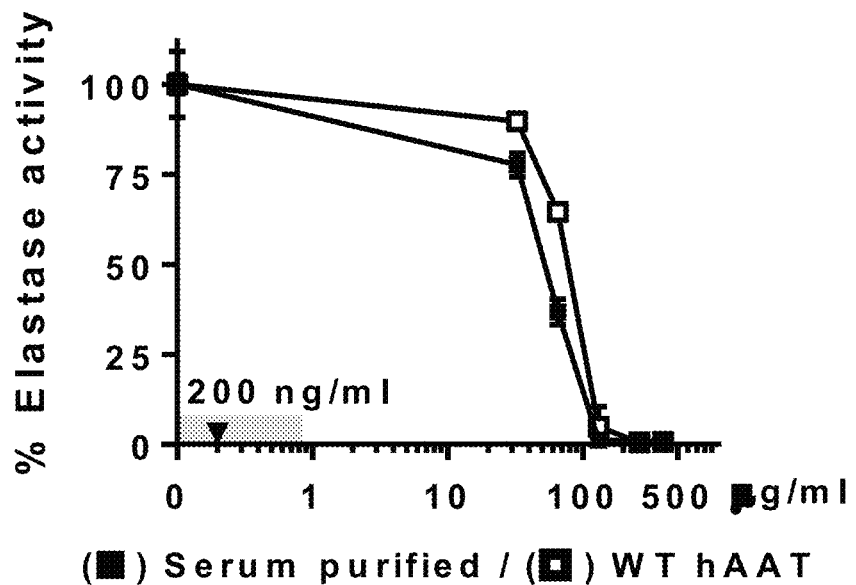
Figure 1G:
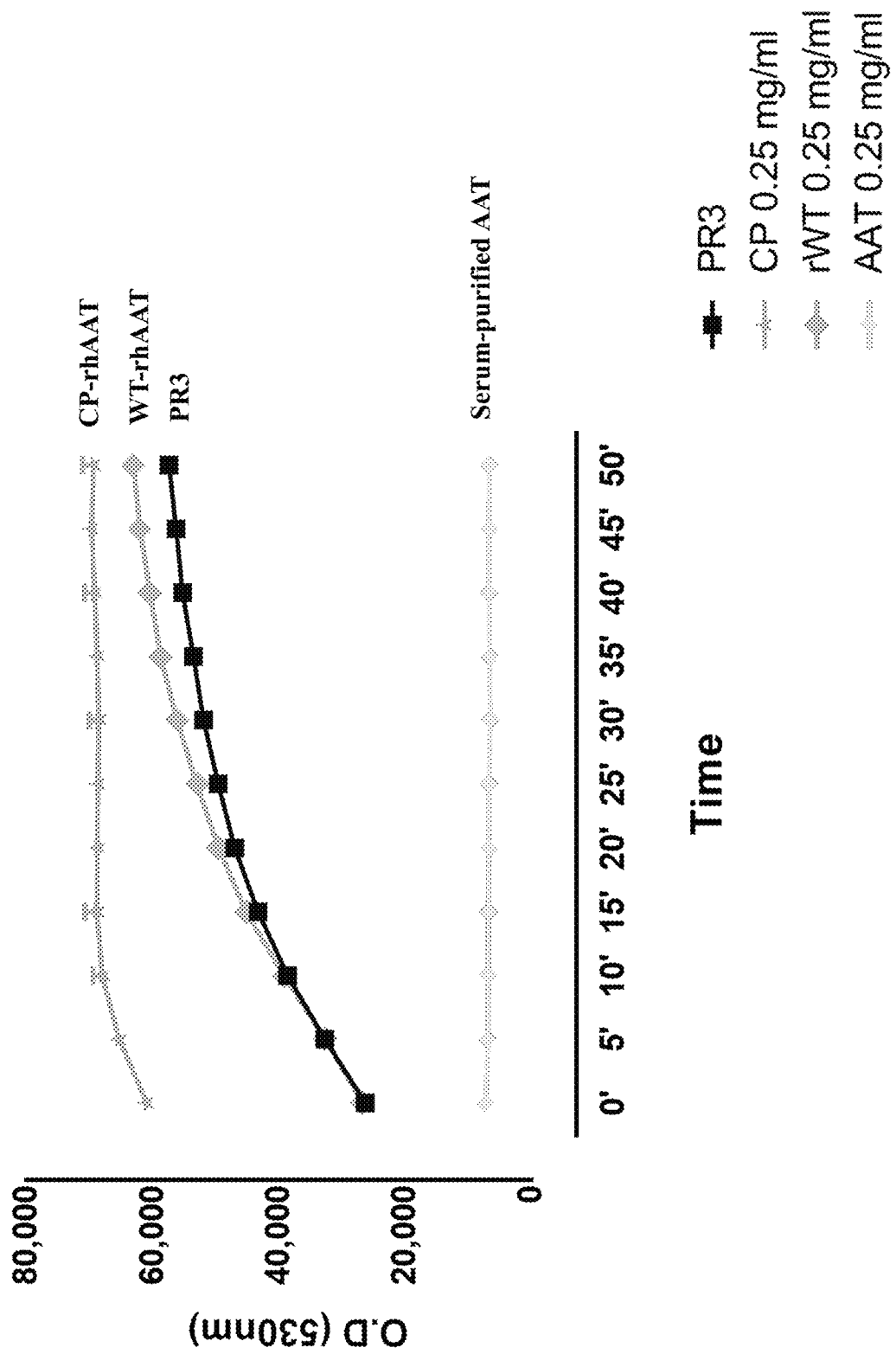

According to neutrophil elastase inhibition assays (FIG. 1F), the WT-rhAAT inhibition profile appears consistent with that of serum-purified hAAT, requiring concentrations in the range of micrograms for inhibition (as opposed to the further experimented 200 ng/ml concentration range, as depicted by arrow). In contrast, the variants C232P (CP), P357C (PC) and P357A (PA) failed to inhibit neutrophil elastase at all tested concentrations. In contrast, WT-rhAAT failed to inhibit proteinase 3 (PR3) in a FRET based inhibition assay (FIG. 1G). PR3 (10 nM) was incubated with serum-purified AAT, WT-rhAAT and CP-rhAAT for 20 minutes, at which point a FRET substrate was added to a final concentration of 2.5 uM and the fluorescence was measured. The FRET substrate only fluoresces upon separation from the quenching molecule, which happens upon cleavage. Serum-purified AAT (0.25 mg/ml) completely inhibited cleavage by PR3, while WT-rhAAT (0.25 mg/ml) had no effect on PR3 activity. This is not surprising, as at this concentration the enzyme had little to no effect on elastase activity. Notably, addition of CP-rhAAT actually enhanced PR3 cleavage such that maximum cleavage occurred after only 10 minutes. Expectedly, inhibition of ADAM17 in an acellular inhibition assay was negative for all formulations of rhAAT as well.

Figure 2A:
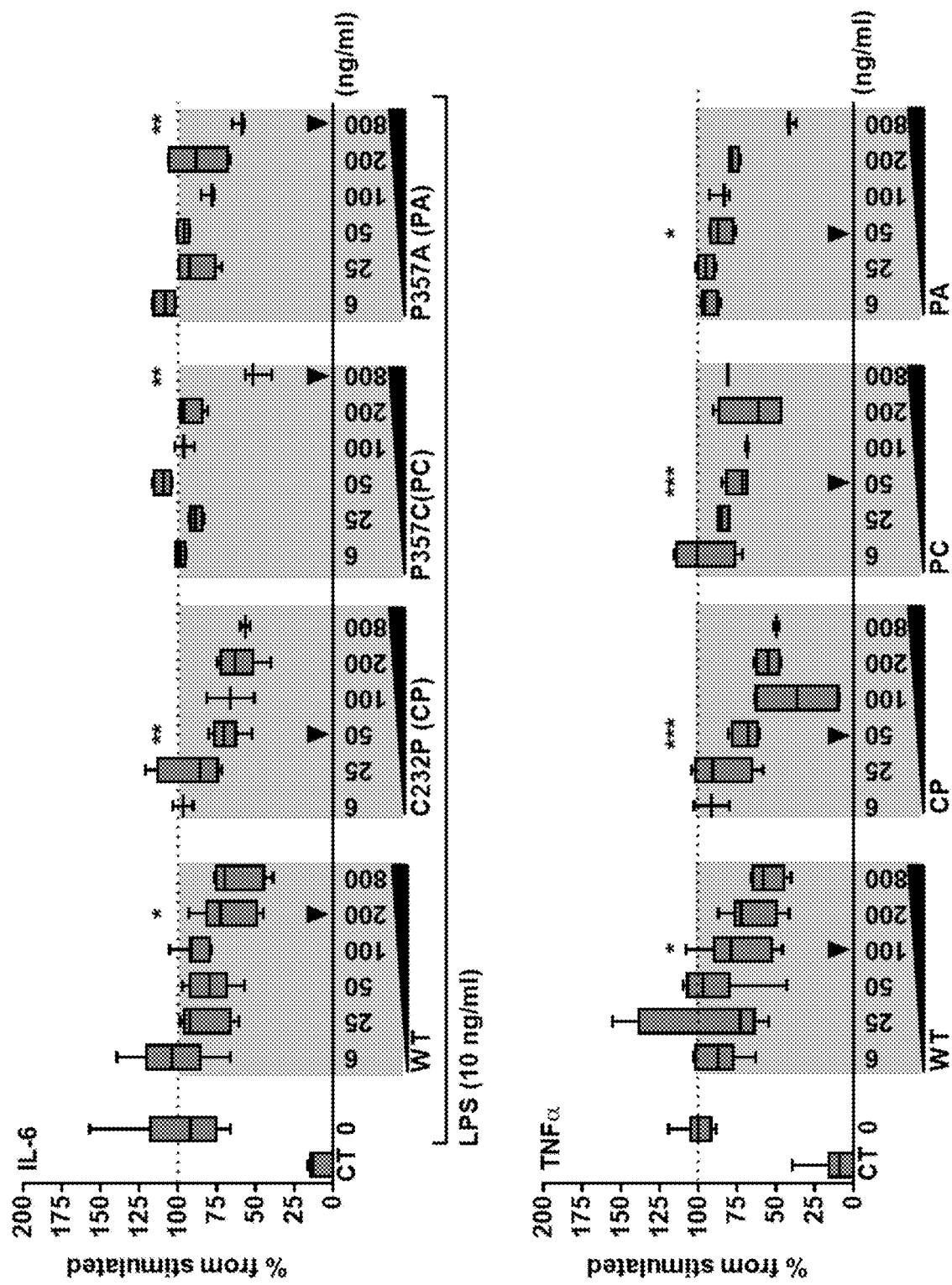
FIGS. 2A-C. rhAAT anti-inflammatory potency variations on leukocyte LPS-responses. (2A) Box plots of cytokine release: BMDMs ($2\times10^5$ per well) with overnight incubation with complete medium containing indicated doses of rhAAT followed by PBS wash and re-incubation with complete medium containing LPS (10 ng/ml, 24 hr). Supernatants analyzed for IL-6 and TNFα concentrations by specific ELISA. Triangle, first statistically significant difference from stimulated sample. (2B) A bar graph of IL-6 secretion from blood cells after LPS stimulation with and without serum-purified AAT and CP-rhAAT. (2C) Bar graphs of membranal activation markers: BMDMs ($5\times10^5$ per well) with overnight incubation with complete medium containing 200 ng/ml rhAAT, followed by LPS addition (10 ng/ml, 24 h) were analyzed for $CD40^{HI}$ and $CD86^{HI}$. $CD11b^+$ and $F4-80^+$ cells were gated for the analysis. Data representative of 4-5 independent experimental repeats. Mean±SEM, *P<0.05, P<0.01, *P<0.001.
Figure 2B:
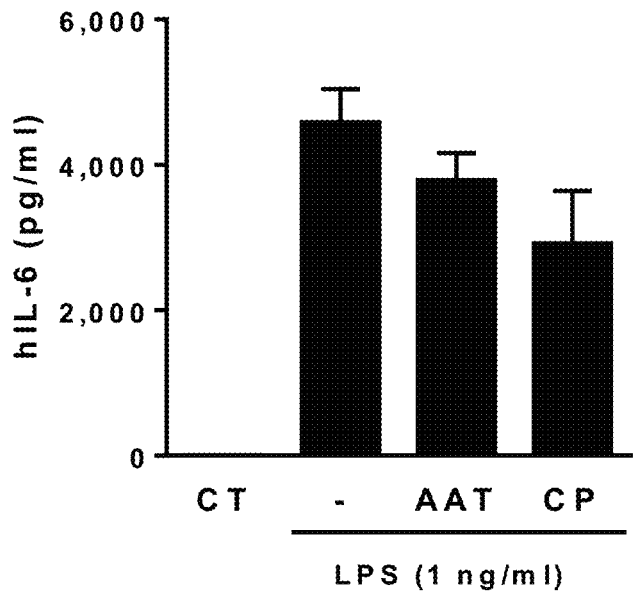
Figure 2C:
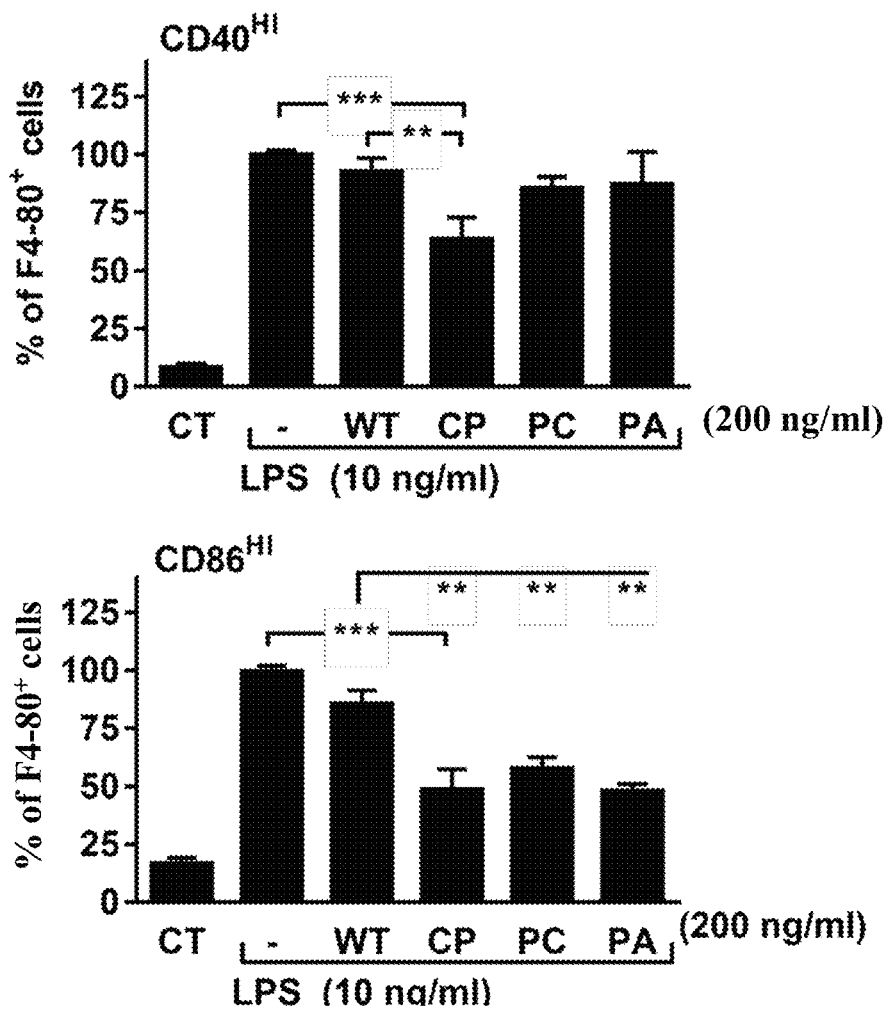

Example 2: Anti-Inflammatory Attributes of rhAAT Variants at Below Protease-Inhibitory Concentrations The response of primary murine bone marrow-derived macrophages (BMDMs) to lipopolysaccharide (LPS) was tested in the presence or absence of hAAT variants. As shown in FIG. 2, the cellular response to LPS included IL-6 and TNFα release (FIG. 2A), and increased expression of CD40 and CD86 (FIG. 2C). WT-rhAAT pretreatment at 200 ng/ml resulted in a significant 31.5% reduction of inducible IL-6 levels. PC and PA pretreatment at this concentration failed to achieve a statistically significant reduction in IL-6 (7% and 12.5% respectively). Notably, CP pretreatment achieved a significant inhibition of inducible IL-6 levels at as little as 50 ng/ml (FIG. 2A, arrowhead). WT-rhAAT pretreatment reached a significant 24.9% decrease in inducible TNFα levels at a concentration of 100 ng/ml. CP, PC and PA all brought about a decline at 50 ng/ml (30.4%, 25.9% and 14.1% respectively) though CP resulted in the greatest decline, with the greatest statistical significance. At 100 ng/ml the effect of CP was even stronger than that of WT (63.7% vs. 24.9% reduction, respectively) though no change was observed for PC or PA at 100 ng/ml.

Similar results were observed when serum-purified AAT was used in place of WT recombinant AAT. Fresh blood from healthy human donors was diluted 1:5 with complete medium, and the diluted blood was treated with PBS, serum-purified AAT (0.5 mg/ml), or CP-hrAAT (10 ug/ml) and then stimulated by LPS two hours later. 18 hours following LPS stimulation the supernatants were collected, and IL-6 secretion was analyzed by ELISA. CP-hrAAT was found to be twice as effective as serum-purified AAT at reducing IL-6 secretion (FIG. 2B).

Based on these observations, the concentration 200 ng/ml was used in evaluating the effect of rhAAT variants on CD40 and CD86 surface expression (FIG. 2C). As shown, changes in CD40 and CD86 displayed a pattern similar to that of released inflammatory cytokines: at 200 ng/ml, WT-rhAAT was ineffective in reducing $CD40^{HI}$ or $CD86^{HI}$ cell population proportions, while CP treatment resulted in significant reduction in $CD40^{HI}$ and $CD86^{HI}$ cell populations (36% and 51%, respectively). Interestingly, CD86 was responsive to PC and PA, causing a reduction of 42% and 51%, respectively, as opposed to CD40 (14% and 13%, respectively).

Figure 3A:
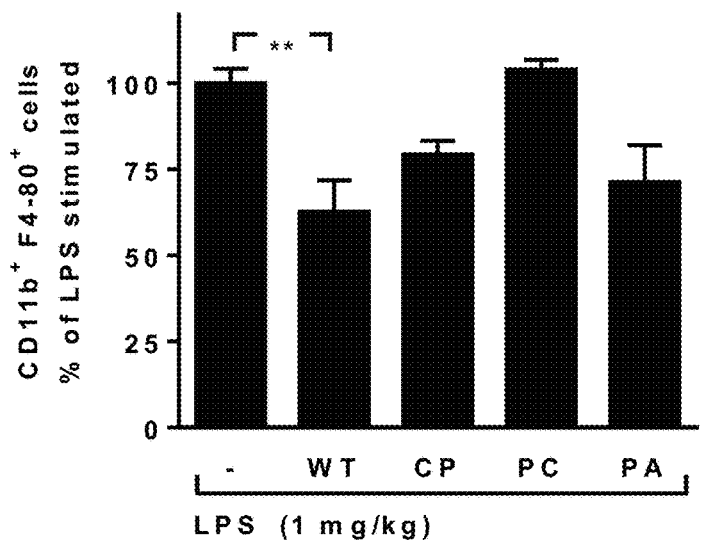
FIGS. 3A-B. rhAAT anti-inflammatory potency variations in sterile peritonitis in vivo models. C57BL/6 mice (n=5 per group) were injected with rhAAT (50 μg per mouse) i.p. and 3 hours afterwards, LPS (1 mg/kg). Peritoneal lavage was performed 24 hours post LPS injection. Bar graphs depicting the results of flow cytometric analysis for (3A) $CD11b^+$ $^F4-80^+$ cells as % of all LPS stimulated cells, (3B) $CD40^{HI}$ and $CD86^{HI}$ cells as % of all P4-80$^+$ cells. CT, control, PBS injection. Mean±SEM, *P<0.05, **P<0.01 compared to LPS stimulated group.
Figure 3B:
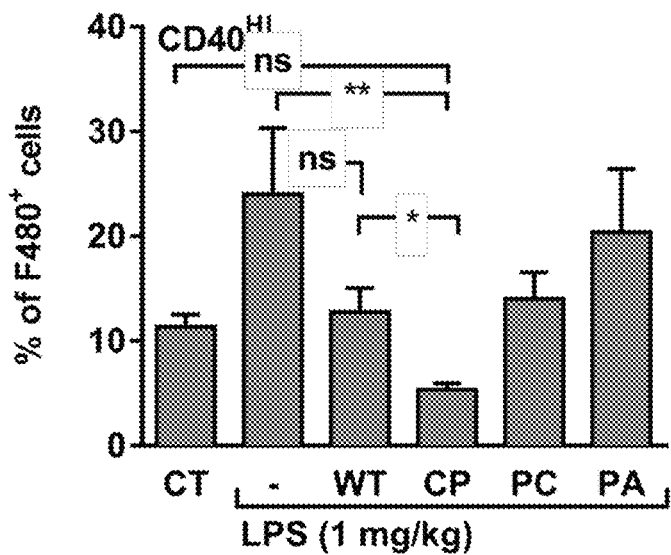
Figure 3B:
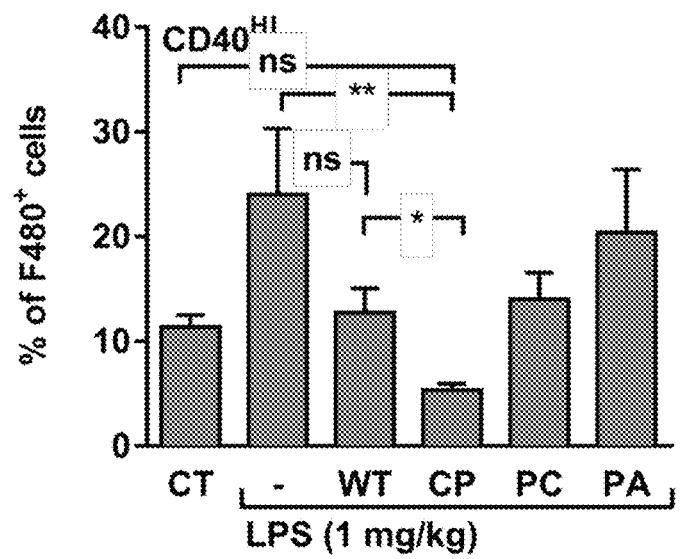

In vivo, the effect of rhAAT on leukocyte responses to LPS was evaluated in a peritoneal LPS-induced sterile inflammatory model, whereby activated infiltrating monocytes are readily depicted upon peritoneal lavage. Here, monocytes were characterized by staining for F4-80 and CD11b (FIG. 3C) and then further tested for the proportion of co-stimulatory activation. As shown in FIG. 3A, animals pretreated with WT-rhAAT exhibited a 36% reduction in $CD11b^+$ $F4-80^+$ cell population size compared to the LPS group (set as 100%). While pretreatment with CP or PA led to a 21% or 29% reduction in CD11b$^+$ F4-80$^+$ cell population, respectively, pretreatment with PC was ineffective in altering cell subtype proportions. The degree of activation of CD11b$^+$ F4-80$^+$ cells was examined (FIG. 3B) and LPS-induced a rise in CD40$^{HI}$ cells such that they were ~24% of the F4-80$^+$ population. Pretreatment with WT-rhAAT resulted in a reduction in CD40$^{HI}$ cells down to ~13% of the population, similar to the reduction down to ~12% observed by pretreatment with the PC variant. In contrast, pretreatment with CP resulted in a greater decline in the proportion of CD40$^{HI}$ cells compared to the LPS group, down to ~5%. PA was ineffective in altering the inducible profile of CD40$^{HI}$ cells. Compared to control untreated animals, CD86$^{HI}$ cell population size was unaffected by in vivo LPS stimulation, leading to ~52% CD86$^{HI}$ of CD11b$^+$ F4-80$^+$ cells; nonetheless, significant reductions in CD86$^{HI}$ cell population size were observed under pretreatment with WT, CP, PC and PA rhAAT compared with LPS treated animals (~31%, ~29%, ~34% and ~36%, respectively)

Example 3: Unique Pharmacokinetics of the CP Variant

Figure 4A:
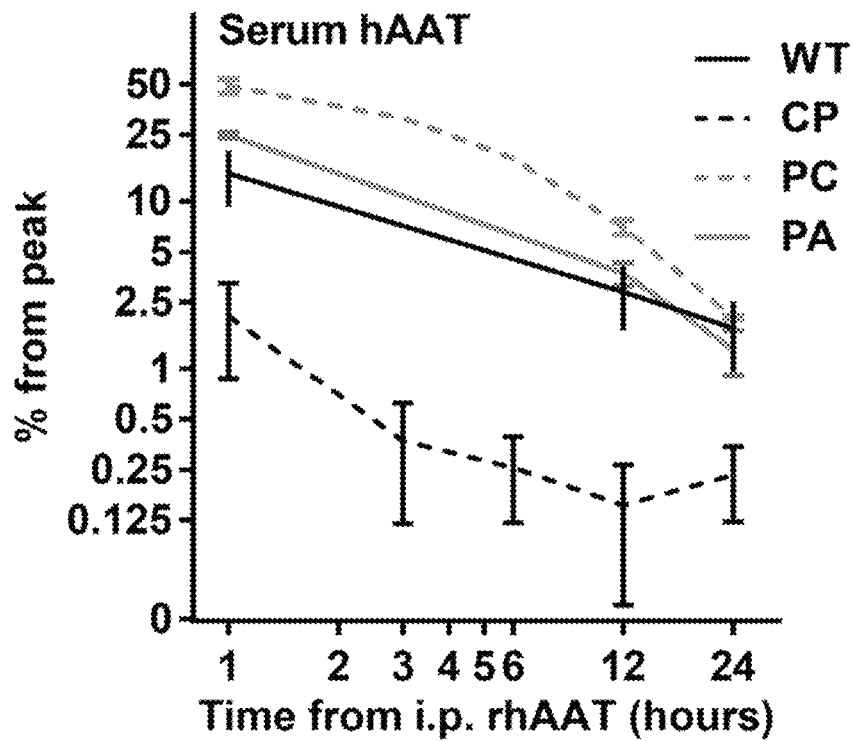
FIGS. 4A-C. Pharmacokinetics. C57BL/6 mice (n=5 per group) were injected with rhAAT i.v. and hAAT concentration analysis by species-specific ELISA from serum samples was performed (1, 12, 24 hrs). (4A) A line graph of hAAT serum concentrations, Mean±SEM. (4B) Bar graph of calculated distribution volume. (4C) Bar graph of calculated half-life time. Data representative of 3 independent experimental repeats., *P<0.05, **P<0.01 compared to WT.
Figure 4B:
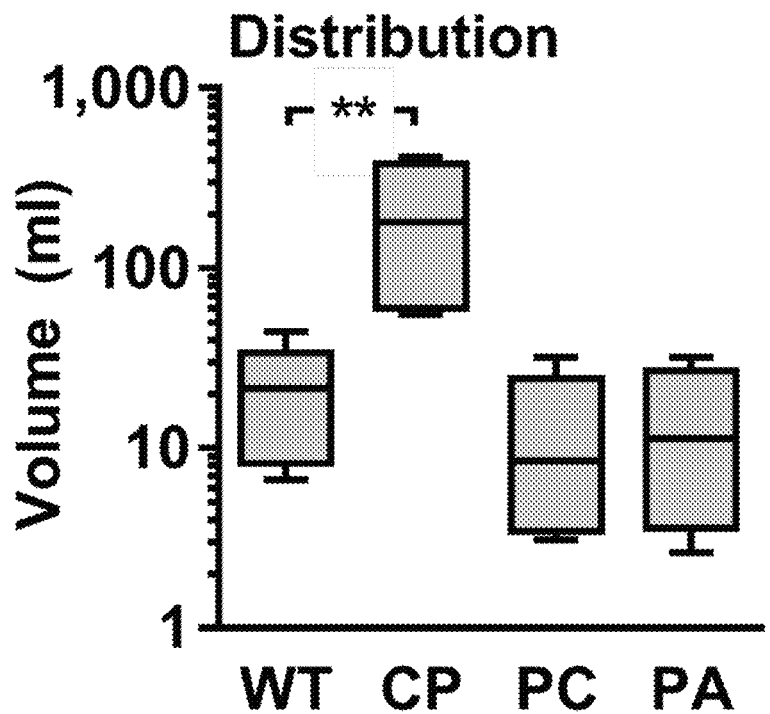
Figure 4C:
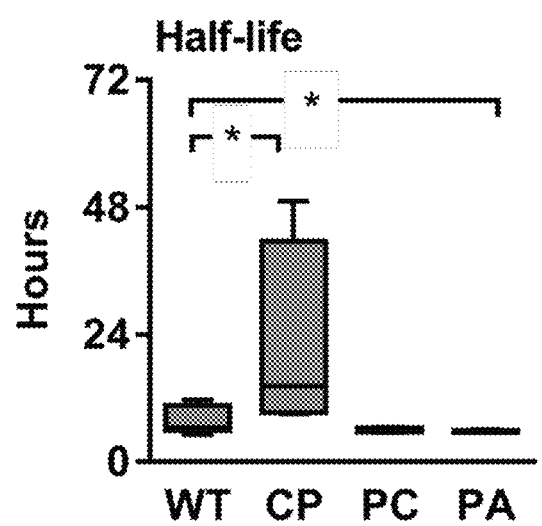

Half-life and distribution volume for each rhAAT variant were calculated based on time-dependent circulating hAAT concentrations, as determined in mice injected with each rhAAT variant (50 μg, i.v). As shown in FIG. 4A the kinetics of the circulating recombinant forms appear uniform between WT, PC and PA. However, the levels of circulating CP were 7.13±0.08-fold lower than in WT-rhAAT as early as 1 hour after injection (FIG. 4A). Accordingly, its distribution volume was calculated to be 9.5±3.0-fold greater than that of WT-rhAAT (FIG. 4B), and its half-life was calculated to be significantly extended (FIG. 4C).

Example 4: Inflammatory Cytokine Expression, Production and Release

Figure 5A:
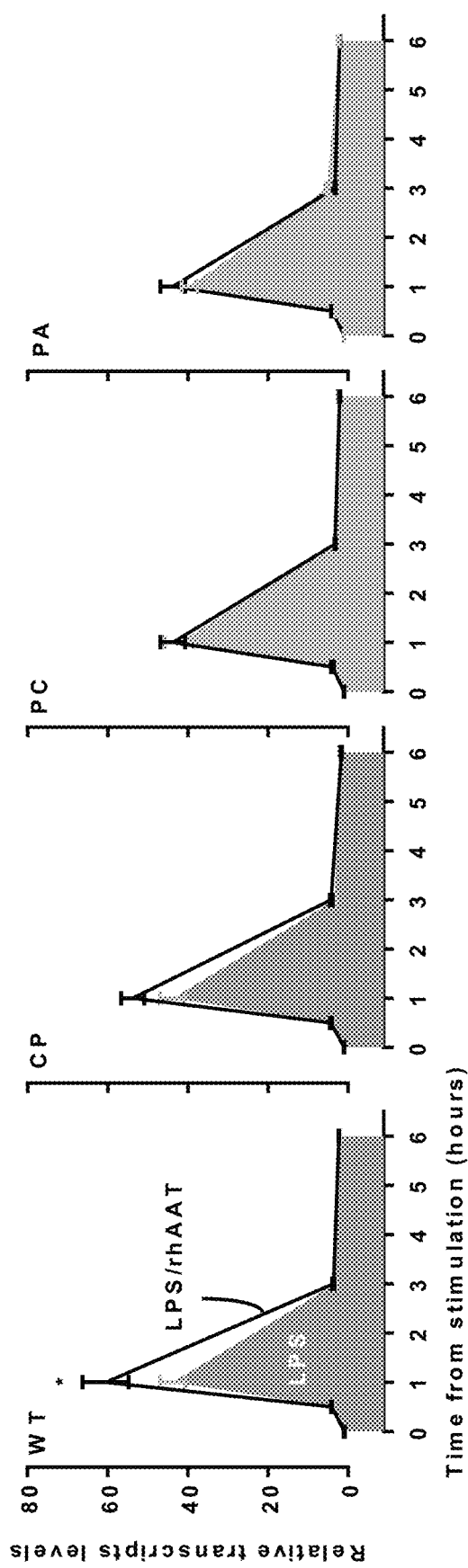
FIGS. 5A-D. rhAAT TNFα transcription, expression and release potency variation. (5A) Line graph of TNFα transcription: Raw 264.7 cells ($0.5\times10^6$ per well) were incubated overnight with complete medium containing 200 ng/ml rhAAT, followed by LPS addition (10 ng/ml, 24 hr), nucleic acids extracted (0.5, 1, 3, 6 hrs) and TNFα transcription assessed by qPCR. Results presented as fold from control. (5B-5C) Box plots of peritoneal macrophages ($3\times10^5$ per well) were incubated overnight with complete medium containing 200 ng/ml rhAAT, followed by LPS addition (10 ng/ml, 24 hr). (5B) Flow cytometric analysis for membrane-associated TNFα. Gate, $CD11b^+$. (5C) Supernatant TNFα analysis by specific ELISA. CT, control, non-stimulated cells. (5D) Line graphs depicting in-vivo sterile peritonitis model serum TNFα levels. C57BL/6 mice (n=5 per group) injected with PBS or rhAAT (50 μg/mouse) i.p. and 3 hours afterwards, LPS (1 mg/kg). TNFα serum analysis by ELISA (1.5, 3 and 24 hrs). Mean±SEM. Data representative of 2 independent experimental repeats. *P<0.05, **P<0.01 compared to LPS stimulated group.
Figure 5B:
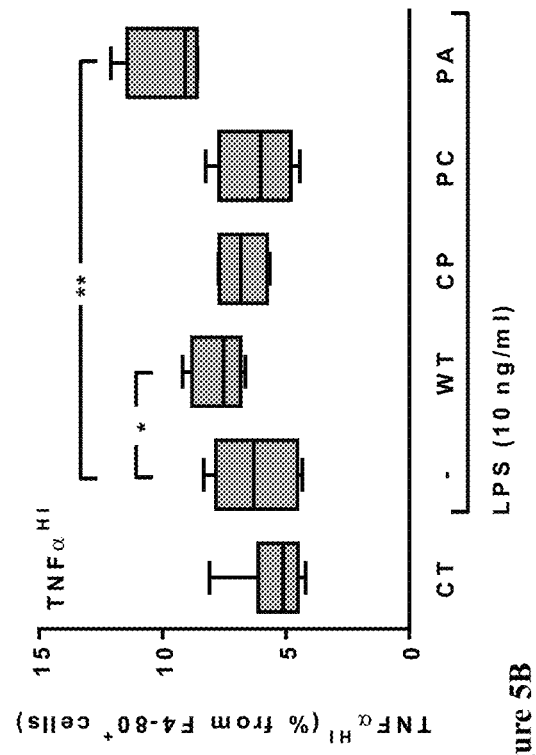
Figure 5C:
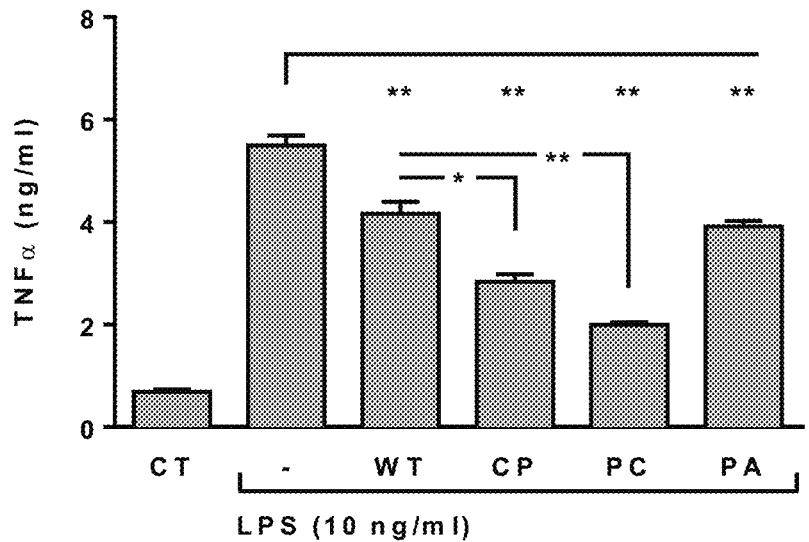
Figure 5D:
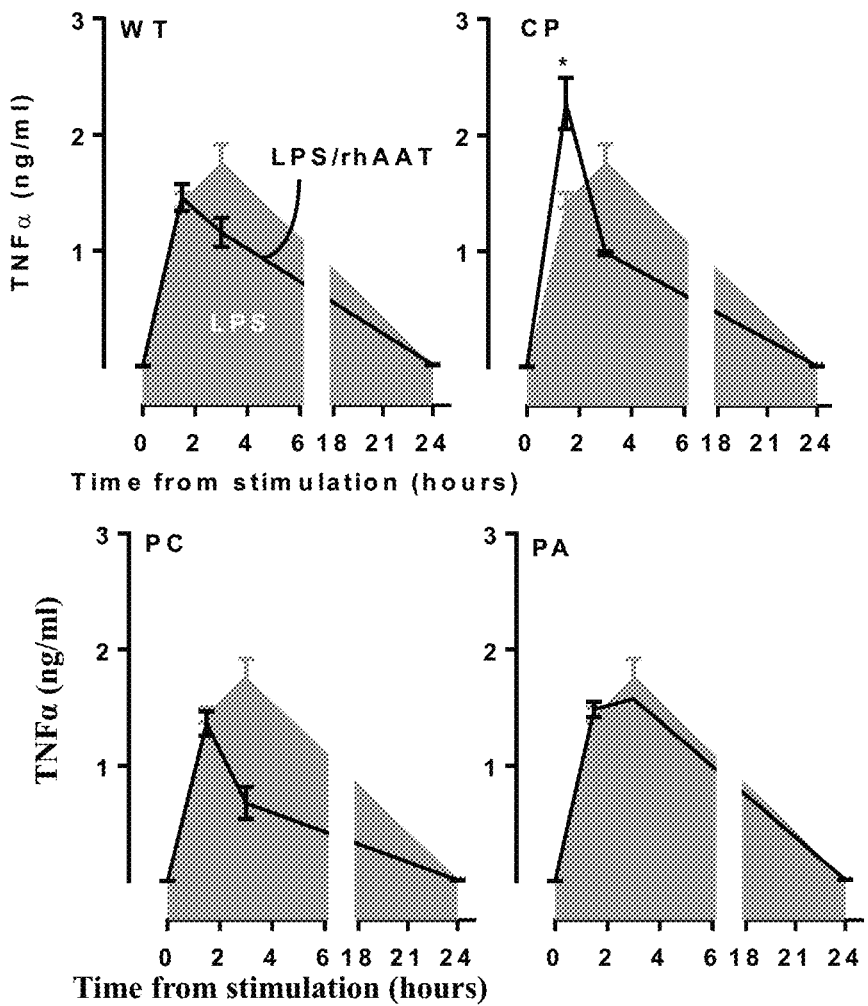

LPS-stimulated RAW264.7 cells were pretreated with rhAAT variants and several aspects of TNFα expression were determined (FIG. 5A transcription, 5B membrane-association, and 5C secreted form in supernatant in vitro). As shown, LPS induced a spike in relative TNFα transcript levels (FIG. 5A, shaded area); accordingly, LPS-treated cultured primary peritoneal cells displayed a rise in TNFα release (FIG. 5C). Similarly, animals injected with LPS exhibited a time-dependent rise in serum TNFα levels (FIG. 5D, shaded area). Membrane-associated TNFα levels (FIG. 5B) displayed no significant change upon LPS stimulation, agreeing with the anticipated dynamic of ADAM17-dependent cleavage of membrane-associated TNFα during inducible TNFα expression. Unexpectedly, pretreatment with WT-rhAAT resulted in a significant rise in TNFα transcript levels one-hour post-stimulation (1.53±0.12-fold from LPS alone, FIG. 5A), coupled with a decline in serum TNFα levels 3 hours post-stimulation (1.5±0.02-fold lower than LPS alone, FIG. 5D).

Interestingly, while the three rhAAT variants displayed no significant effect on LPS-induced TNFα transcription levels (FIG. 5A), pretreatment with CP resulted in a significant early narrow spike in serum TNFα levels (FIG. 5D). PC displayed a pattern of inhibition similar to that of WT-rhAAT, and PA did not exert a significant effect on LPS-stimulated TNFα serum levels (FIG. 5D). In vitro (FIG. 5C), the levels of secreted TNFα were consistent with in vivo findings, in that treatment with WT, CP, PC or PA brought about a decline in soluble TNFα concentrations, most effectively by CP and PC variants.

Expression of TNFα without the secretion of its soluble form could be caused by inhibition of ADAM17 activity; such a process would result in elevated levels of membrane-associated non-cleaved TNFα. Here, membrane-associated TNFα levels were evaluated after pretreatment with each of the rhAAT variants (FIG. 5B). Pretreatment with WT-rhAAT resulted in a significant increase in membrane-associated TNFα, corresponding to the 24% lower soluble TNFα under the same conditions (FIG. 5C). However, membrane-associated and soluble TNFα responded differentially to the various variants; while the effect of CP and PC on the membrane associated form was minimal (FIG. 5B), soluble TNFα levels were reduced by 48% and 63%, respectively (FIG. 5C). Interestingly, PA was the sole variant which resulted in a significant rise in membrane-associated TNFα levels (FIG. 5B). However, this rise was coupled with only a 29% decrease in soluble TNFα level, similar to that seen in WT rhAAT pretreatment (FIG. 5C). The overall effect of CP, compared to WT rhAAT, appears to involve a minor shift in transcript levels and rapidly declining soluble TNFα levels with only a minimal change in membrane-associated TNFα; at the same time, the first evidence of circulating TNFα in vivo is pushed up to the 1-hr zone, temporarily exhibiting higher TNFα levels in the serum, than LPS alone.

Example 4: Improved Wound Healing with CP rhAAT

Figure 6A:
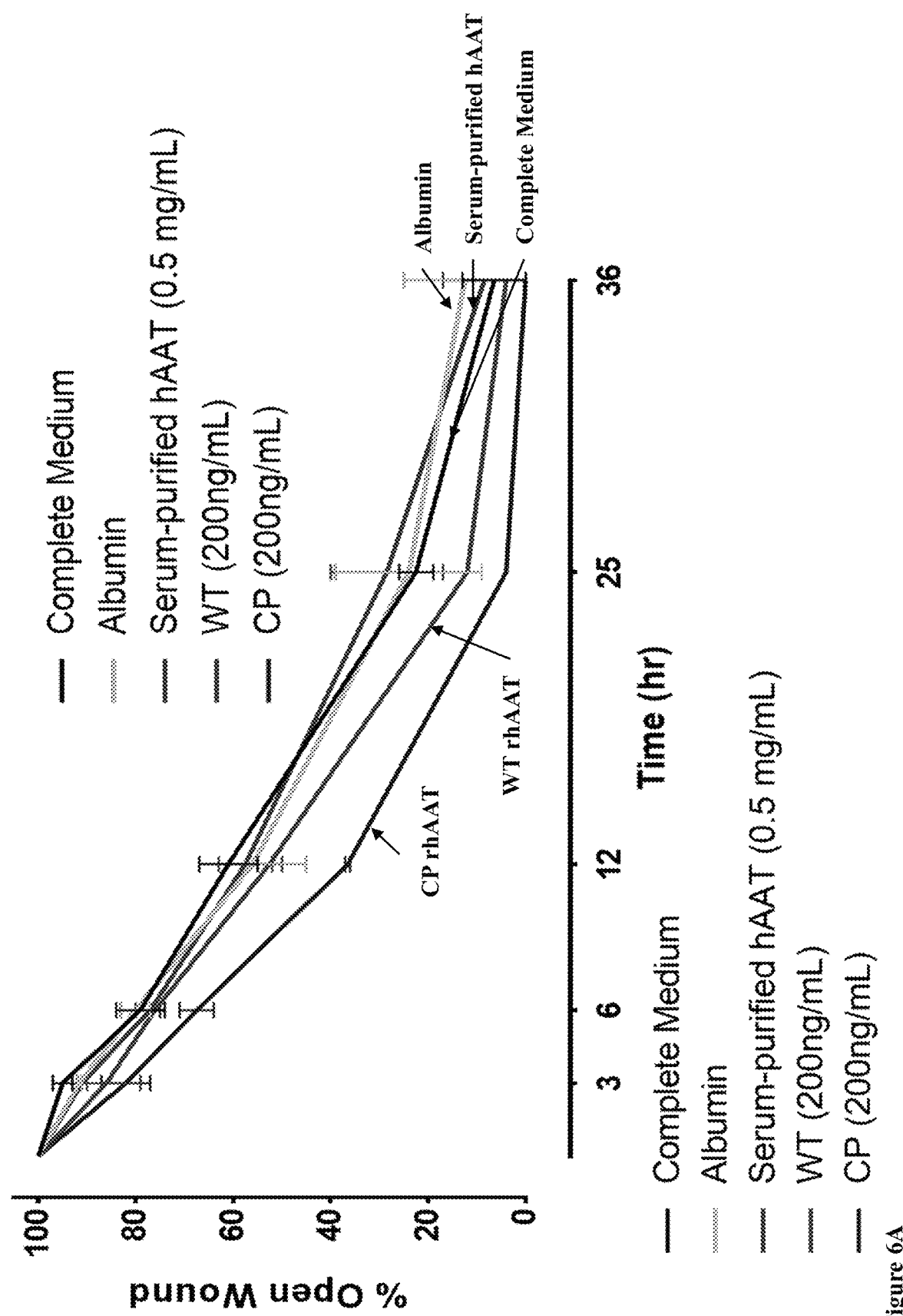
FIGS. 6A-B. rhAAT enhances wound healing. (6A) Line graph of the percentage of the open wound remaining after performance of the scratch test. (6B) Line graph of the percentage of the wound area remaining after wound infliction in mice.

Alpha 1 antitrypsin has a known role in wound healing; the CP rhAAT variant was therefore tested in its ability to stimulate wound healing and closure. A549 cells were seeded at a concentration 0.2×10$^^$ cells/well in a 24 well plate. A scratch was applied to the plate using a 200 ul pipette tip and the wound area was monitored by photography for 36 hours. Wound areas were quantified at 3, 6, 12, 25 and 36 hours post scratch using the Fiji software package. Addition of serum purified hAAT (0.5 mg/ml) had no effect on wound closure, as compared to control cells that received only medium, or albumin (FIG. 6A). WT rhAAT induced increased closing of the scratch area starting at 12 hours. CP rhAAT showed by far the greatest impact, with increased closing at every time point examined, and a superior closing at 25 hours to that observed in all other conditions at 36 hours.

Figure 6B:
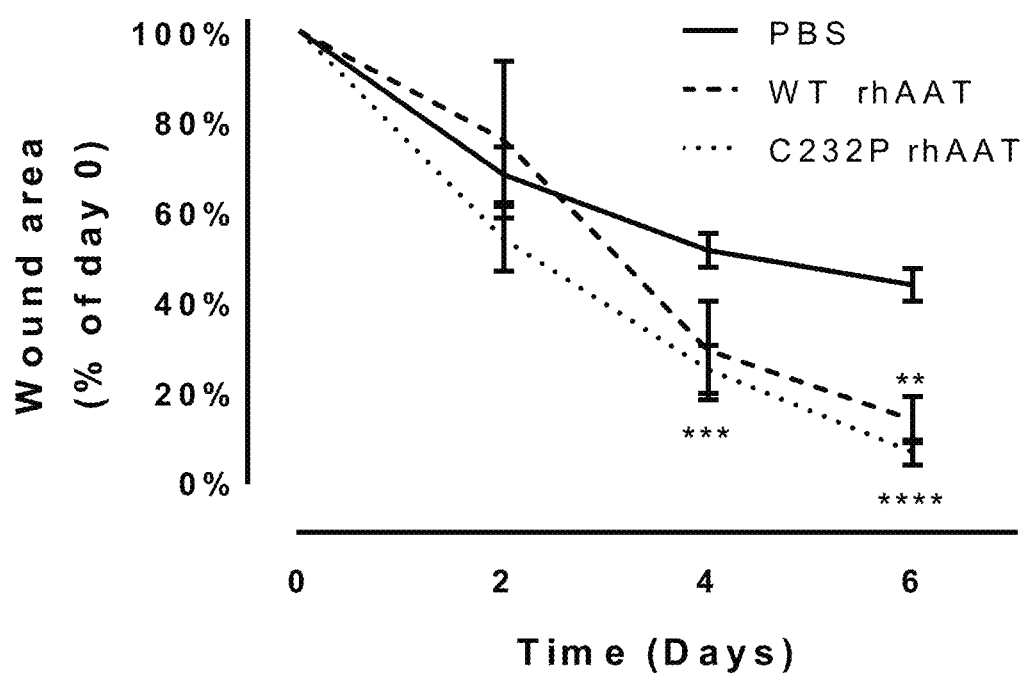

A similar experiment was next performed in mice. Four 5-mm full-thickness skin wounds were punctured on the dorsal skin of anesthetized C57BL/6 mice (n=7). The wound borders were injected with 100 ul of PBS, PBS containing WT-rhAAT (1 ug/ul) or PBS containing CP-rhAAT (1 ug/ul). Wound dimensions were recorded on days 2, 4 and 6 by digital imaging and quantified using the ImageJ program (FIG. 6B). Both WT-rhAAT and CP-rhAAT improved the rate of healing, but this improvement was observed earlier with the CP variant (improvement at day 2, while there was none with WT), and the CP variant produced overall better healing at all time points.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. An isolated alpha 1-antitrypsin (AAT) variant comprising the amino acid of SEQ ID NO: 1, wherein X is proline.

2. The isolated AAT variant of claim 1, having a greater anti-inflammatory property compared to recombinant human alpha 1-antitrypsin (rhAAT) protein (SEQ ID NO: 2) or serum purified human alpha 1-antitrypsin (hAAT).

3. The isolated AAT variant of claim 2, wherein said anti-inflammatory property is reducing secretion of a pro-inflammatory cytokine.

4. The isolated AAT variant of claim 3, wherein said pro-inflammatory cytokine is IL-6.

5. A pharmaceutical composition comprising the isolated AAT variant of claim 1 and a pharmaceutically acceptable carrier or excipient.

6. A method of treating, ameliorating or preventing a wound or an inflammatory disease or disorder in a subject in need thereof, the method comprising administering to said subject a therapeutically effective amount of the pharmaceutical composition of claim 5, thereby treating, ameliorating or preventing the inflammatory disease or disorder in said subject.

7. The method of claim 6, wherein the inflammatory disease or disorder is selected from the group consisting of: diabetes, allogenic and xenogeneic transplantation, graft-versus-host disease, myocardial infarction, radiation exposure, chronic fatigue syndrome, bacterial infection, inflammatory bowel disease, rheumatoid arthritis, liver disease, radiation exposure, osteoporosis, multiple sclerosis, neuromyelitis optica, organ injury in patients undergoing cardiac surgery, ischemia-reperfusion associated injuries of the heart and lung, and osteoporosis.

8. The method of claim 6, wherein the therapeutically effective amount is within a dosage range of 0.05-60 mg/kg.

9. The method of claim 6, wherein the wound is in the skin of said subject.

10. A method for increasing a therapeutic property in a protein comprising an alpha 1-antitrypsin, comprising mutating said protein comprising an alpha 1-antitrypsin to obtain a mutated protein comprising the isolated AAT variant of claim 1, thereby increasing a therapeutic property in a protein comprising an alpha 1-antitrypsin.

11. The method of claim 10, wherein said therapeutic property is selected from an anti-inflammatory property and a wound healing property.

12. The method of claim 11, wherein said anti-inflammatory property is selected from reducing secretion of a pro-inflammatory cytokine and reducing activation of macrophages.

* * * * *

SEQUENCE LISTING

<160> NUMBER OF SEQ ID NOS: 5

<210> SEQ ID NO 1
<211> LENGTH: 394
<212> TYPE: PRT
<213> ORGANISM: Homo sapiens
<220> FEATURE:
<221> NAME/KEY: MISC_FEATURE
<222> LOCATION: (232)..(232)
<223> OTHER INFORMATION: Xaa can be any naturally occurring amino acid
      other than cysteine, or can be absent.

<400> SEQUENCE: 1

```
Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Xaa Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
```

```
                   340                 345                 350
Leu Glu Ala Ile Pro Met Ser Ile Pro Pro Glu Val Lys Phe Asn Lys
            355                 360                 365

Pro Phe Val Phe Leu Met Ile Glu Gln Asn Thr Lys Ser Pro Leu Phe
        370                 375                 380

Met Gly Lys Val Val Asn Pro Thr Gln Lys
385                 390

<210> SEQ ID NO 2
<211> LENGTH: 394
<212> TYPE: PRT
<213> ORGANISM: Homo sapiens

<400> SEQUENCE: 2

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320
```

```
Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
            355                 360                 365

Pro Phe Val Phe Leu Met Ile Glu Gln Asn Thr Lys Ser Pro Leu Phe
370                 375                 380

Met Gly Lys Val Val Asn Pro Thr Gln Lys
385                 390

<210> SEQ ID NO 3
<211> LENGTH: 394
<212> TYPE: PRT
<213> ORGANISM: Artificial Sequence
<220> FEATURE:
<223> OTHER INFORMATION: Synthetic

<400> SEQUENCE: 3

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
    195                 200                 205

His Val Asp Gln Val Thr Thr Val Lys Val Pro Met Met Lys Arg Leu
210                 215                 220

Gly Met Phe Asn Ile Gln His Pro Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285
```

```
Pro Lys Leu Ser Ile Thr Gly Thr Tyr Asp Leu Lys Ser Val Leu Gly
            290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
                    340                 345                 350

Leu Glu Ala Ile Pro Met Ser Ile Pro Pro Glu Val Lys Phe Asn Lys
                355                 360                 365

Pro Phe Val Phe Leu Met Ile Glu Gln Asn Thr Lys Ser Pro Leu Phe
370                 375                 380

Met Gly Lys Val Val Asn Pro Thr Gln Lys
385                 390

<210> SEQ ID NO 4
<211> LENGTH: 394
<212> TYPE: PRT
<213> ORGANISM: Artificial Sequence
<220> FEATURE:
<223> OTHER INFORMATION: Synthetic

<400> SEQUENCE: 4

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
                20                  25                  30

Phe Ala Phe Ser Leu Tyr Arg Gln Leu Ala His Gln Ser Asn Ser Thr
            35                  40                  45

Asn Ile Phe Phe Ser Pro Val Ser Ile Ala Thr Ala Phe Ala Met Leu
        50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255
```

-continued

```
Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Cys Met Ser Ile Pro Pro Glu Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys
385                 390
```

<210> SEQ ID NO 5
<211> LENGTH: 394
<212> TYPE: PRT
<213> ORGANISM: Artificial Sequence
<220> FEATURE:
<223> OTHER INFORMATION: Synthetic

<400> SEQUENCE: 5

```
Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220
```

```
Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
                260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
        290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
                340                 345                 350

Leu Glu Ala Ile Ala Met Ser Ile Pro Pro Glu Val Lys Phe Asn Lys
        355                 360                 365

Pro Phe Val Phe Leu Met Ile Glu Gln Asn Thr Lys Ser Pro Leu Phe
        370                 375                 380

Met Gly Lys Val Val Asn Pro Thr Gln Lys
385                 390
```